(12) United States Patent
Handique et al.

(10) Patent No.: US 10,466,160 B2
(45) Date of Patent: Nov. 5, 2019

(54) SYSTEM AND METHOD FOR RETRIEVING AND ANALYZING PARTICLES

(71) Applicant: DeNovo Sciences, Inc., Plymouth, MI (US)

(72) Inventors: Kalyan Handique, Plymouth, MI (US); Austin Payne, Plymouth, MI (US); Vishal Sharma, Plymouth, MI (US); Kyle Gleason, Plymouth, MI (US); Priyadarshini Gogoi, Plymouth, MI (US); Karthik Ganesan, Plymouth, MI (US); Brian Boniface, Plymouth, MI (US); Will Chow, Plymouth, MI (US)

(73) Assignee: Celsee Diagnostics, Inc., Plymouth, MI (US)

( * ) Notice: Subject to any disclaimer, the term of this patent is extended or adjusted under 35 U.S.C. 154(b) by 147 days.

(21) Appl. No.: 15/815,532

(22) Filed: Nov. 16, 2017

(65) Prior Publication Data

US 2018/0088023 A1  Mar. 29, 2018

Related U.S. Application Data

(63) Continuation-in-part of application No. 15/720,194, filed on Sep. 29, 2017, now Pat. No. 9,925,538, and
(Continued)

(51) Int. Cl.
*G01N 15/14* (2006.01)
*G01N 15/10* (2006.01)
(Continued)

(52) U.S. Cl.
CPC .... *G01N 15/1484* (2013.01); *B01L 3/502715* (2013.01); *B01L 3/502761* (2013.01);
(Continued)

(58) Field of Classification Search
CPC ..... B01L 2200/0652; B01L 2200/0668; B01L 2300/0636; B01L 2300/0654;
(Continued)

(56) References Cited

U.S. PATENT DOCUMENTS

| 644,134 A | 2/1900 | Gastineau |
| 4,551,435 A | 11/1985 | Liberti et al. |

(Continued)

FOREIGN PATENT DOCUMENTS

| EP | 2414548 A2 | 2/2012 |
| WO | 035909 | 5/2003 |

(Continued)

OTHER PUBLICATIONS

"Supplemental information from Tan et al. PNAS (2007) 104. (Year: 2007)".

(Continued)

*Primary Examiner* — Jennifer Wecker
(74) *Attorney, Agent, or Firm* — Jeffrey Schox

(57) ABSTRACT

A system and method for isolating and analyzing single cells, including: a substrate having a broad surface; a set of wells defined at the broad surface of the substrate, and a set of channels, defined by the wall, that fluidly couple each well to at least one adjacent well in the set of wells; and fluid delivery module defining an inlet and comprising a plate, removably coupled to the substrate, the plate defining a recessed region fluidly connected to the inlet and facing the broad surface of the substrate, the fluid delivery module comprising a cell capture mode.

19 Claims, 10 Drawing Sheets

Related U.S. Application Data a continuation-in-part of application No. 15/657,553, filed on Jul. 24, 2017, now Pat. No. 10,345,219, said application No. 15/720,194 is a continuation of application No. 15/431,977, filed on Feb. 14, 2017, now Pat. No. 9,802,193, application No. 15/815,532, which is a continuation-in-part of application No. 15/430,833, filed on Feb. 13, 2017, said application No. 15/657,553 is a continuation of application No. 15/333,420, filed on Oct. 25, 2016, now Pat. No. 9,746,413, said application No. 15/430,833 is a continuation of application No. 15/199,245, filed on Jun. 30, 2016, now Pat. No. 9,612,199, said application No. 15/431,977 is a continuation of application No. 14/863,191, filed on Sep. 23, 2015, now Pat. No. 9,610,581, said application No. 15/333,420 is a continuation of application No. 14/607,918, filed on Jan. 28, 2015, now Pat. No. 9,513,195, said application No. 15/199,245 is a continuation of application No. 14/208,458, filed on Mar. 13, 2014, now Pat. No. 9,404,864, said application No. 14/863,191 is a continuation of application No. 14/208,298, filed on Mar. 13, 2014, now Pat. No. 9,174,216, said application No. 14/607,918 is a continuation of application No. 13/557,510, filed on Jul. 25, 2012, now Pat. No. 9,103,754.

(60) Provisional application No. 62/545,251, filed on Aug. 14, 2017, provisional application No. 62/423,322, filed on Nov. 17, 2016, provisional application No. 61/902,431, filed on Nov. 11, 2013, provisional application No. 61/894,150, filed on Oct. 22, 2013, provisional application No. 61/829,528, filed on May 31, 2013, provisional application No. 61/779,049, filed on Mar. 13, 2013, provisional application No. 61/779,090, filed on Mar. 13, 2013, provisional application No. 61/513,785, filed on Aug. 1, 2011.

(51) Int. Cl.

| | |
|---|---|
| *G01N 1/20* | (2006.01) |
| *B01L 3/00* | (2006.01) |
| *C12M 1/00* | (2006.01) |
| *G01N 1/28* | (2006.01) |
| *G01N 1/40* | (2006.01) |
| *G01N 35/00* | (2006.01) |
| *G01N 35/10* | (2006.01) |
| *G06K 9/00* | (2006.01) |
| *G06K 9/20* | (2006.01) |
| *G01N 15/00* | (2006.01) |
| *B01L 3/02* | (2006.01) |

(52) U.S. Cl.
CPC ............... *C12M 47/04* (2013.01); *G01N 1/20* (2013.01); *G01N 1/28* (2013.01); *G01N 1/40* (2013.01); *G01N 1/405* (2013.01); *G01N 1/4077* (2013.01); *G01N 15/1475* (2013.01); *G01N 35/00029* (2013.01); *G01N 35/1011* (2013.01); *G06K 9/00127* (2013.01); *G06K 9/209* (2013.01); *G06K 9/2027* (2013.01); *G06K 9/2036* (2013.01); *B01L 3/021* (2013.01); *B01L 3/502746* (2013.01); *B01L 2200/0652* (2013.01); *B01L 2200/0668* (2013.01); *B01L 2300/0636* (2013.01); *B01L 2300/0654* (2013.01); *B01L 2300/0672* (2013.01); *B01L 2300/0816* (2013.01); *B01L 2300/0819* (2013.01); *B01L 2300/0848* (2013.01); *B01L 2300/0877* (2013.01); *B01L 2300/168* (2013.01); *B01L 2400/086* (2013.01); *G01N 2015/0065* (2013.01); *G01N 2015/1006* (2013.01); *G01N 2015/149* (2013.01); *G01N 2035/00158* (2013.01); *G01N 2035/1039* (2013.01)

(58) Field of Classification Search
CPC ..... B01L 2300/0672; B01L 2300/0816; B01L 2300/0819; B01L 2300/0848; B01L 2300/0877; B01L 2300/168; B01L 2400/086; B01L 3/021; B01L 3/502715; B01L 3/502746; B01L 3/502761; C12M 47/04; G01N 15/1475; G01N 15/1484; G01N 1/20; G01N 1/28; G01N 1/40; G01N 1/405; G01N 1/4077; G01N 2015/0065; G01N 2015/1006; G01N 2015/149; G01N 2035/00158; G01N 2035/1039; G01N 35/00029; G01N 35/1011; G06K 9/00127; G06K 9/2027; G06K 9/2036; G06K 9/209

See application file for complete search history.

(56) References Cited

U.S. PATENT DOCUMENTS

| | | |
|---|---|---|
| 4,710,635 A | 12/1987 | Chupp |
| 5,266,269 A | 11/1993 | Niiyama et al. |
| 5,491,343 A | 2/1996 | Brooker |
| 5,851,488 A | 12/1998 | Saul et al. |
| 5,883,370 A | 3/1999 | Walker et al. |
| 5,888,370 A | 3/1999 | Becker et al. |
| 5,993,630 A | 11/1999 | Becker et al. |
| 5,993,632 A | 11/1999 | Becker et al. |
| 6,016,712 A | 1/2000 | Warden et al. |
| 6,127,177 A | 10/2000 | Toner et al. |
| 6,133,030 A | 10/2000 | Bhatia et al. |
| 6,150,180 A | 11/2000 | Parce et al. |
| 6,174,683 B1 | 1/2001 | Hahn |
| 6,221,663 B1 | 4/2001 | Bhatia et al. |
| 6,228,624 B1 | 5/2001 | Terstappen |
| 6,281,008 B1 | 8/2001 | Komai et al. |
| 6,287,832 B1 | 9/2001 | Becker et al. |
| 6,365,362 B1 | 4/2002 | Terstappen et al. |
| 6,410,724 B1 | 6/2002 | Dejean et al. |
| 6,433,134 B1 | 8/2002 | Patron et al. |
| 6,525,997 B1 | 2/2003 | Narayanaswami et al. |
| 6,563,634 B2 | 5/2003 | Shimada et al. |
| 6,613,525 B2 | 9/2003 | Nelson et al. |
| 6,623,983 B1 | 9/2003 | Terstappen et al. |
| 6,641,708 B1 | 11/2003 | Becker et al. |
| 6,645,731 B2 | 11/2003 | Terstappen et al. |
| 6,692,952 B1 | 2/2004 | Braff et al. |
| 6,790,330 B2 | 9/2004 | Gascoyne et al. |
| 6,821,484 B1 | 11/2004 | Gregersen |
| 6,861,259 B2 | 3/2005 | Columbus |
| 6,960,449 B2 | 11/2005 | Wang et al. |
| 7,008,789 B2 | 3/2006 | Gambini et al. |
| 7,035,170 B2 | 4/2006 | Narayanaswami et al. |
| 7,046,357 B2 | 5/2006 | Weinberger et al. |
| 7,148,492 B2 | 12/2006 | Loney et al. |
| 7,172,866 B2 | 2/2007 | Hahn et al. |
| 7,198,901 B1 | 4/2007 | Rachlin |
| 7,217,520 B2 | 5/2007 | Tsinberg et al. |
| 7,238,521 B2 | 7/2007 | Hahn et al. |
| 7,248,352 B2 | 7/2007 | Hamamatsu et al. |
| 7,258,990 B2 | 8/2007 | Falcovitz-Gerassi et al. |
| 7,266,777 B2 | 9/2007 | Scott et al. |
| 7,294,468 B2 | 11/2007 | Bell et al. |
| 7,316,897 B2 | 1/2008 | Bisconte et al. |
| 7,332,288 B2 | 2/2008 | Terstappen et al. |
| 7,338,760 B2 | 3/2008 | Gong et al. |
| 7,354,389 B2 | 4/2008 | Kureshy et al. |
| 7,439,062 B2 | 10/2008 | Bhatt et al. |

(56) References Cited

U.S. PATENT DOCUMENTS

| | | |
|---|---|---|
| 7,449,558 B2 | 11/2008 | Yao et al. |
| 7,449,778 B2 | 11/2008 | Sander |
| 7,507,528 B2 | 3/2009 | Albert et al. |
| 7,588,672 B2 | 9/2009 | Unger et al. |
| 7,595,157 B2 | 9/2009 | Tsinberg |
| 7,597,528 B2 | 10/2009 | Rodi |
| 7,604,777 B2 | 10/2009 | Columbus |
| 7,638,464 B2 | 12/2009 | Fagnani et al. |
| 7,695,956 B2 | 4/2010 | Tsinberg et al. |
| 7,704,322 B2 | 4/2010 | Hansen et al. |
| 7,710,563 B2 | 5/2010 | Betzig et al. |
| 7,738,320 B2 | 6/2010 | Taha |
| 7,763,704 B2 | 7/2010 | Ding et al. |
| 7,815,863 B2 | 10/2010 | Kagan et al. |
| 7,858,757 B2 | 12/2010 | Hollmann et al. |
| 7,863,012 B2 | 1/2011 | Rao et al. |
| 7,901,950 B2 | 3/2011 | Connelly et al. |
| 7,964,349 B2 | 6/2011 | Bell et al. |
| 8,008,032 B2 | 8/2011 | Forsyth et al. |
| 8,013,298 B2 | 9/2011 | Khursheed |
| 8,021,614 B2 | 9/2011 | Huang et al. |
| 8,103,080 B2 | 1/2012 | George et al. |
| 8,105,769 B2 | 1/2012 | Bell et al. |
| 8,105,780 B2 | 1/2012 | Su et al. |
| 8,131,053 B2 | 3/2012 | Ortyn et al. |
| 8,158,410 B2 | 4/2012 | Tang et al. |
| 8,174,698 B2 | 5/2012 | Peter et al. |
| 8,175,371 B2 | 5/2012 | George et al. |
| 8,186,913 B2 | 5/2012 | Toner et al. |
| 8,232,112 B2 | 7/2012 | Willson et al. |
| 8,252,517 B2 | 8/2012 | Thomas et al. |
| 8,293,524 B2 | 10/2012 | Ionescu-Zanetti et al. |
| 8,304,230 B2 | 11/2012 | Toner et al. |
| 8,329,422 B2 | 12/2012 | Rao et al. |
| 8,372,579 B2 | 2/2013 | Toner et al. |
| 8,372,584 B2 | 2/2013 | Shoemaker et al. |
| 8,406,498 B2 | 3/2013 | Ortyn et al. |
| 8,465,916 B2 | 6/2013 | Bell et al. |
| 8,628,923 B2 | 1/2014 | Hamilton et al. |
| 8,658,418 B2 | 2/2014 | Daridon |
| 8,680,025 B2 | 3/2014 | Cooney |
| 8,730,479 B2 | 5/2014 | Ness et al. |
| 8,765,454 B2 | 7/2014 | Zhou et al. |
| 8,771,609 B2 | 7/2014 | Ehben et al. |
| 8,802,367 B2 | 8/2014 | Taniguchi et al. |
| 8,936,945 B2 | 1/2015 | Handique et al. |
| 8,986,988 B2 | 3/2015 | Karnik et al. |
| 9,110,026 B2 | 8/2015 | Collins |
| 9,133,499 B2 | 9/2015 | Di Carlo et al. |
| 9,145,540 B1 | 9/2015 | Deutsch et al. |
| 9,174,216 B2 | 11/2015 | Handique et al. |
| 9,188,586 B2 | 11/2015 | Fan et al. |
| 9,194,001 B2 | 11/2015 | Brenner |
| 9,200,245 B2 | 12/2015 | Deutsch et al. |
| 9,201,060 B2 | 12/2015 | Voldman et al. |
| 9,249,459 B2 | 2/2016 | Hamilton et al. |
| 9,260,753 B2 | 2/2016 | Xie et al. |
| 9,290,808 B2 | 3/2016 | Fodor et al. |
| 9,290,809 B2 | 3/2016 | Fodor et al. |
| 9,304,065 B2 | 4/2016 | Fowler et al. |
| 9,315,768 B2 | 4/2016 | Vrouwe et al. |
| 9,315,857 B2 | 4/2016 | Fu et al. |
| 9,329,170 B2 | 5/2016 | Clarke et al. |
| 9,364,829 B2 | 6/2016 | Heid et al. |
| 9,410,201 B2 | 8/2016 | Hindson et al. |
| 9,429,500 B2 | 8/2016 | Fowler et al. |
| 9,506,845 B2 | 11/2016 | Fowler et al. |
| 9,507,609 B2 | 11/2016 | Glazer et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,610,581 B2 | 4/2017 | Handique et al. |
| 9,637,799 B2 | 5/2017 | Fan et al. |
| 9,701,998 B2 | 7/2017 | Hindson et al. |
| 9,707,562 B2 | 7/2017 | Handique et al. |
| 9,708,659 B2 | 7/2017 | Fodor et al. |
| 9,757,707 B2 | 9/2017 | Husain et al. |
| 9,802,193 B2 | 10/2017 | Handique et al. |
| 9,840,732 B2 | 12/2017 | Anderson et al. |
| 9,845,502 B2 | 12/2017 | Fodor et al. |
| 9,850,483 B2 | 12/2017 | Clarke et al. |
| 9,952,126 B2 | 4/2018 | Fowler et al. |
| 9,995,662 B2 | 6/2018 | Husain et al. |
| 2004/0106130 A1 | 6/2004 | Besemer et al. |
| 2004/0229349 A1 | 11/2004 | Daridon |
| 2005/0014201 A1 | 1/2005 | Deuthsch |
| 2006/0128006 A1 | 6/2006 | Gerhardt et al. |
| 2006/0257992 A1 | 11/2006 | McDevitt et al. |
| 2008/0003224 A1 | 1/2008 | Fong et al. |
| 2008/0014589 A1 | 1/2008 | Link et al. |
| 2008/0090239 A1 | 4/2008 | Shoemaker et al. |
| 2008/0206751 A1 | 8/2008 | Squirrell et al. |
| 2009/0061450 A1 | 3/2009 | Hunter |
| 2009/0081773 A1 | 3/2009 | Kaufman |
| 2009/0317836 A1 | 12/2009 | Kuhn et al. |
| 2010/0261179 A1 | 10/2010 | Betley et al. |
| 2010/0291584 A1 | 11/2010 | Tseng et al. |
| 2010/0304978 A1 | 12/2010 | Deng et al. |
| 2011/0053151 A1 | 3/2011 | Hansen et al. |
| 2011/0117634 A1 | 5/2011 | Halamish et al. |
| 2011/0227558 A1 | 9/2011 | Mannion et al. |
| 2012/0071355 A9 | 3/2012 | Cooney |
| 2012/0129190 A1 | 5/2012 | Chiu et al. |
| 2012/0156675 A1 | 6/2012 | Luerssen et al. |
| 2012/0164679 A1 | 6/2012 | Vrouwe et al. |
| 2013/0171628 A1 | 7/2013 | Di et al. |
| 2014/0173443 A1 | 6/2014 | Hawkins, III et al. |
| 2014/0213487 A1 | 7/2014 | Freudenthal et al. |
| 2014/0315237 A1 | 10/2014 | Masujima et al. |
| 2014/0357511 A1* | 12/2014 | Handique ............ C12Q 1/6886 506/9 |
| 2014/0370612 A1* | 12/2014 | Bassler ................ G01N 15/147 436/94 |
| 2015/0089359 A1 | 3/2015 | Brisebois |
| 2015/0093306 A1 | 4/2015 | Thorne et al. |
| 2015/0133319 A1 | 5/2015 | Fu et al. |
| 2015/0376609 A1 | 12/2015 | Hindson et al. |
| 2016/0024572 A1 | 1/2016 | Shishkin et al. |
| 2016/0024761 A1 | 1/2016 | Korb |
| 2016/0053253 A1 | 2/2016 | Salathia et al. |
| 2016/0060621 A1 | 3/2016 | Agresti et al. |
| 2016/0130649 A1 | 5/2016 | Xie et al. |
| 2016/0209319 A1 | 7/2016 | Adalsteinsson et al. |
| 2016/0251714 A1 | 9/2016 | Conant et al. |
| 2016/0289669 A1 | 10/2016 | Fan et al. |
| 2016/0314242 A1 | 10/2016 | Schnall-Levin et al. |
| 2017/0044525 A1 | 2/2017 | Kaper et al. |
| 2017/0307502 A1 | 10/2017 | Mason et al. |
| 2017/0320038 A1 | 11/2017 | Husain et al. |
| 2017/0321252 A1 | 11/2017 | Hindson et al. |
| 2017/0335385 A1 | 11/2017 | Hindson et al. |
| 2017/0356027 A1 | 12/2017 | Hindson et al. |
| 2018/0030515 A1 | 2/2018 | Regev et al. |
| 2018/0037942 A1 | 2/2018 | Fu |
| 2018/0051321 A1 | 2/2018 | Hindson et al. |
| 2018/0080075 A1 | 3/2018 | Brenner et al. |
| 2018/0094298 A1 | 4/2018 | Hindson et al. |
| 2018/0094312 A1 | 4/2018 | Hindson et al. |
| 2018/0105808 A1 | 4/2018 | Mikkelsen et al. |
| 2018/0112266 A1 | 4/2018 | Hindson et al. |
| 2018/0127744 A1 | 5/2018 | Hu et al. |
| 2018/0127823 A1 | 5/2018 | Shekhar et al. |
| 2018/0274027 A1 | 9/2018 | Hindson et al. |
| 2018/0282804 A1 | 10/2018 | Hindson et al. |

FOREIGN PATENT DOCUMENTS

| | | |
|---|---|---|
| WO | 098696 | 9/2006 |
| WO | 2010120818 A2 | 10/2010 |

(56) References Cited

FOREIGN PATENT DOCUMENTS

WO          2018013723 A1     1/2018
WO          2018058073 A2     3/2018

OTHER PUBLICATIONS

Guo, P. et al. Microfluidic capture and release of bacteria in a conical nanopore array. Lab Chip. vol. 12, pp. 558-561, 2012, published online Nov. 2011.

Lindstrom, Sara (Royal Institute of Technology, Stockholm, Sweden, 2009, pp. 1-80).

Sugio et al. (Sensors and Actuators, B99, 2004, pp. 156-162).

Seale, K. T. et al. "Mirrored pyramidal wells for simultaneous multiple vantage point microscopy." Journal of Microscopy (2008) 232 1-6. (Year: 2008).

Sugio, Yoshihiro et al. "An agar-based on-chip neural-cell-cultivation system for stepwise control of network pattern generation during cell cultivation." Sensors and Actuators B (2004) 99 156-162. (Year: 2004).

Tan, Wei-Heang et al. "A trap-and-release integrated microfluidic system for dynamic microarray applications." PNAS (2007) 104 1146-1151. (Year: 2007).

"Guo, P. et al. Microfluidic capture and release of bacteria in a conical nanopore array. Lab Chip. vol. 12, pp. 558-561, 2012, published online Nov. 2011.", Jun. 30, 2017 00:00:00.0.

\* cited by examiner

FIGURE 1A
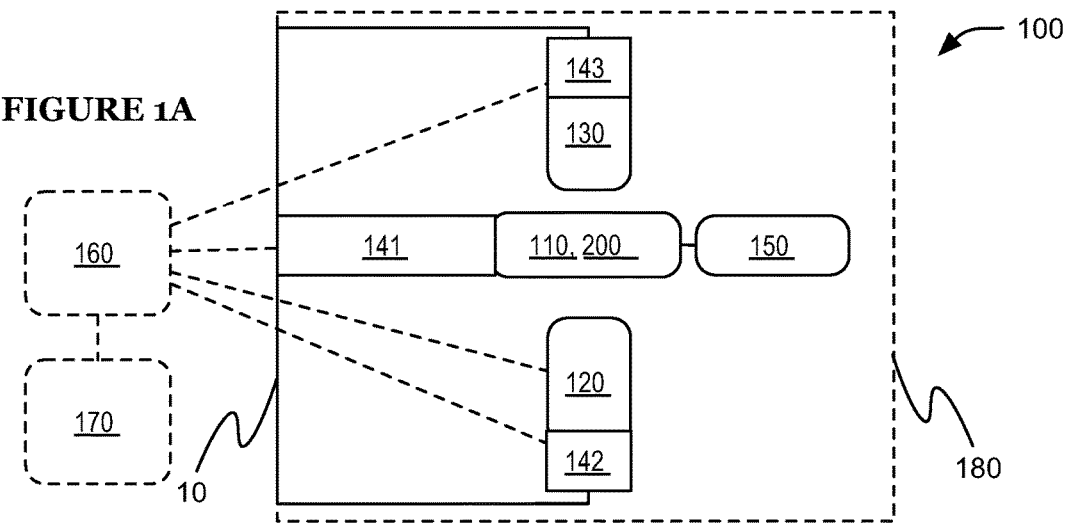
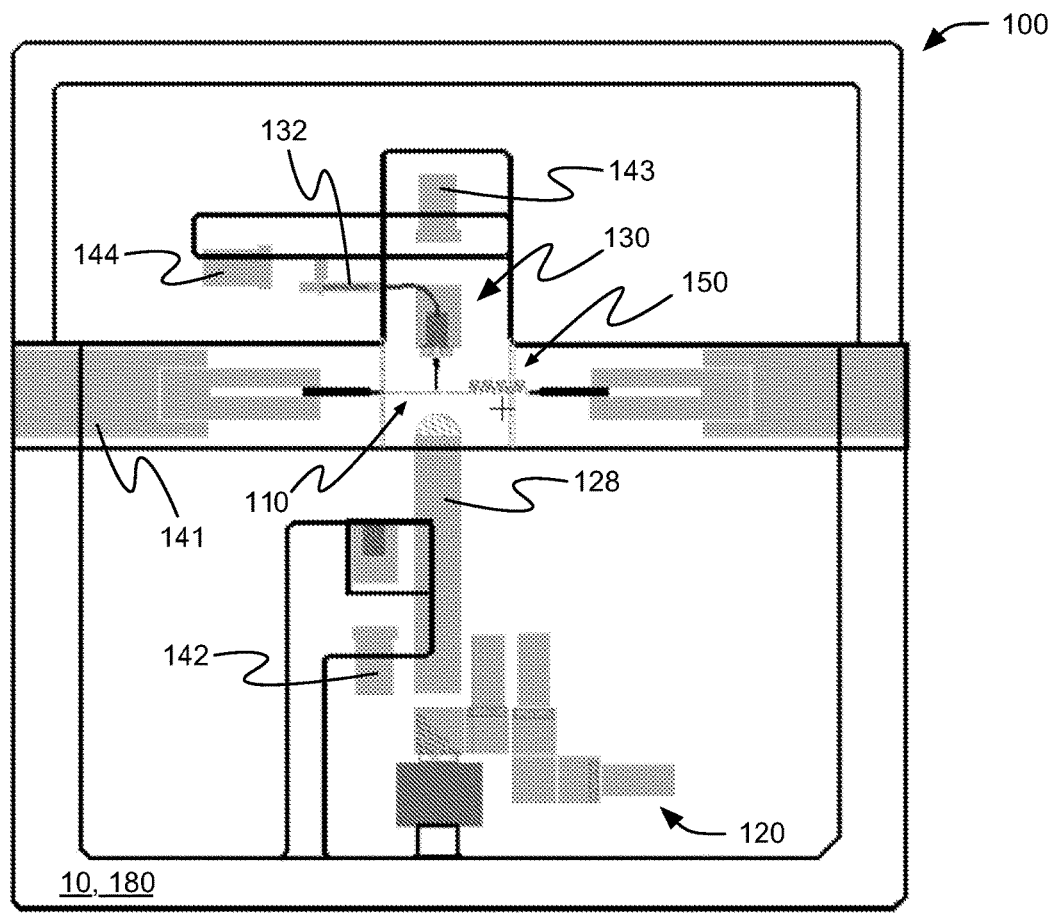
FIGURE 1B

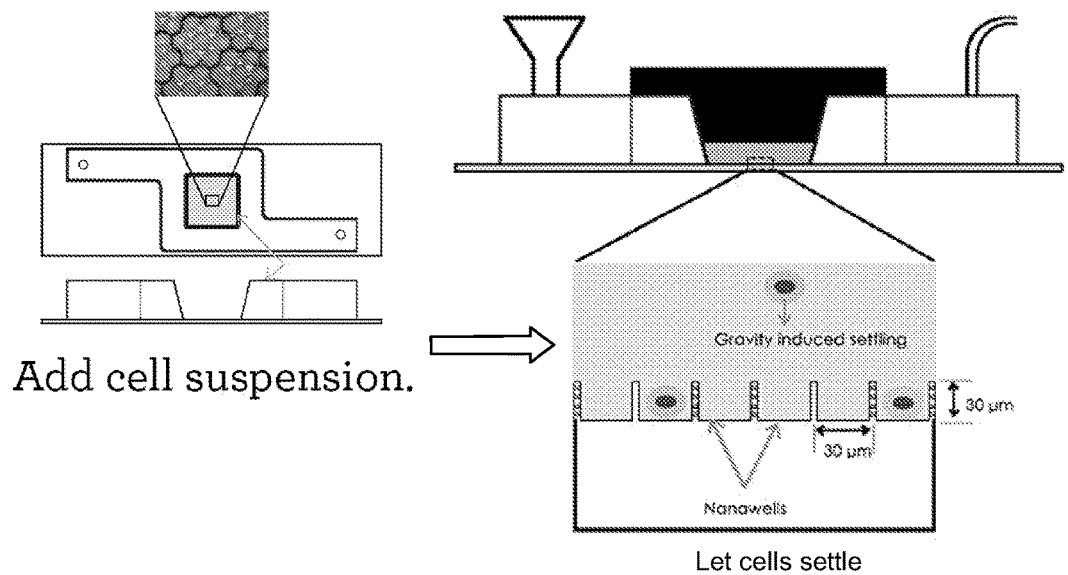
FIGURE 9
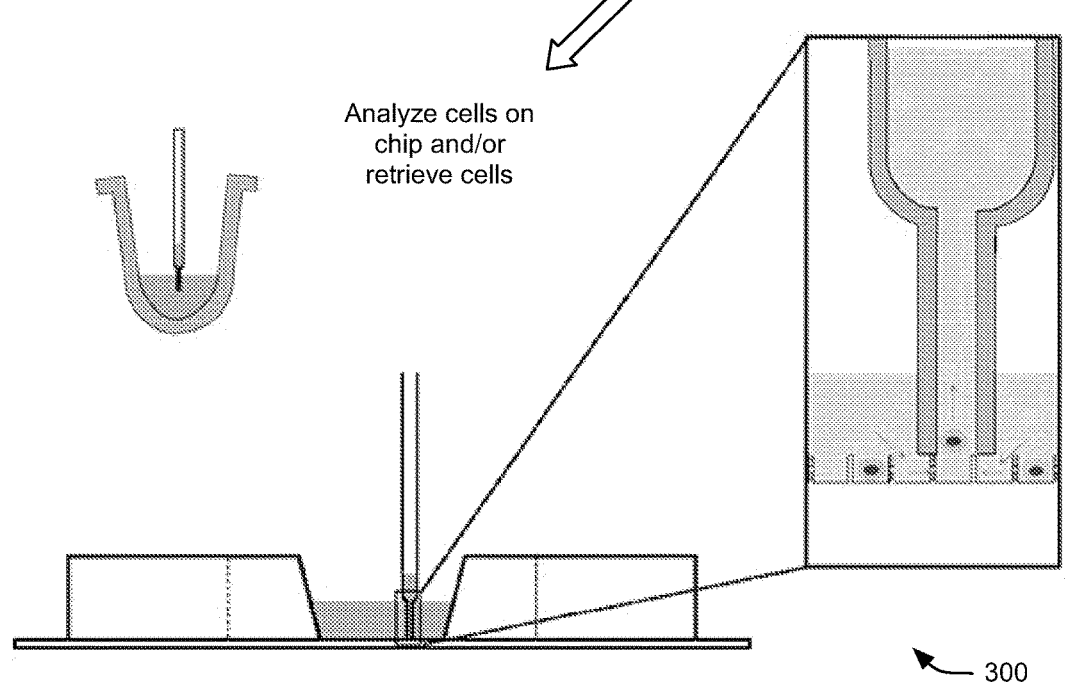

SYSTEM AND METHOD FOR RETRIEVING AND ANALYZING PARTICLES

CROSS-REFERENCE TO RELATED APPLICATIONS

This application is a continuation-in-part of U.S. patent application Ser. No. 15/657,553, filed 24 Jul. 2017, which is a continuation of U.S. patent application Ser. No. 5/333,420, filed 25 Oct. 2016, which is a is a continuation of U.S. patent application Ser. No. 14/607,918, filed 28 Jan. 2015, which is a continuation of U.S. patent application Ser. No. 13/557,510, filed 25 Jul. 2012, and claims the benefit of U.S. Provisional Application Ser. No. 61/513,785 filed on 1 Aug. 2011, which are all incorporated in their entirety by this reference.

This application is also a continuation-in-part of U.S. patent application Ser. No. 15/720,194, filed 29 Sep. 2017, which is a continuation of U.S. patent application Ser. No. 15/431,977, filed 14 Feb. 2017, which is a continuation of U.S. patent application Ser. No. 14/863,191 (now U.S. Pat. No. 9,610,581), filed 23 Sep. 2015, which is a continuation of U.S. patent application Ser. No. 14/208,298 (now U.S. Pat. No. 9,174,216), filed 13 Mar. 2014, which claims the benefit of U.S. Provisional Application Ser. No. 61/894,150, filed on 22 Oct. 2013, U.S. Provisional Application Ser. No. 61/829,528, filed on 31 May 2013, and U.S. Provisional Application Ser. No. 61/779,049, filed on 13 Mar. 2013, which are all incorporated herein in their entirety by this reference.

This application is also a continuation-in-part of U.S. patent application Ser. No. 15/430,833, filed 13 Feb. 2017, which is a continuation of U.S. patent application Ser. No. 15/199,245, filed 30 Jun. 2016, which is a continuation of U.S. patent application Ser. No. 14/208,458, filed 13 Mar. 2014, which claims the benefit of U.S. Provisional Application Ser. No. 61/902,431, filed on 11 Nov. 2013, and U.S. Provisional Application Ser. No. 61/779,090, filed on 13 Mar. 2013, all of which are incorporated herein in their entirety by this reference.

This application claims the benefit of U.S. Provisional Application Ser. No. 62/423,322, filed 17 Nov. 2016, and U.S. Provisional Application Ser. No. 62/545,251, filed 14 Aug. 2017, each of which is incorporated herein in its entirety by this reference.

This application is also related to U.S. patent application Ser. No. 15/442,222, filed 24 Feb. 2017, which is incorporated herein in its entirety by this reference.

TECHNICAL FIELD

This invention relates generally to the particle analysis field, and more specifically to a new and useful system and method for retrieving and analyzing particles within the particle analysis field.

BACKGROUND

With an increased interest in cell-specific drug testing, diagnosis, and other assays, systems that allow for individual cell isolation, identification, and retrieval are becoming more desirable within the field of cellular analysis. Furthermore, with the onset of personalized medicine, low-cost, high fidelity cellular analysis systems are becoming highly desirable. However, preexisting cell and other particle capture systems suffer from various shortcomings that prevent widespread adoption for cell-specific testing. For example, flow cytometry requires that the cell be simultaneously identified and sorted, and limits cell observation to the point at which the cell is sorted. Flow cytometry fails to allow for multiple analyses of the same cell within a single flow cytometry workflow, and does not permit arbitrary cell subpopulation sorting. Conventional microfluidic devices typically fail to allow for subsequent cell removal without cell damage, and only capture the cells expressing the specific antigen; non-expressing cells, which could also be desired, are not captured by these systems. Such loss of cell viability can preclude live-cell assays from being performed on sorted or isolated cells. Cellular filters can separate sample components based on size without significant cell damage, but suffer from clogging and do not allow for specific cell identification, isolation of individual cells, and retrieval of identified individual cells. Other technologies in this field are further limited in their ability to allow multiplex assays to be performed on individual cells, while minimizing sample preparation steps and overly expensive instrumentation.

Thus, there is a need in the particle sorting field to create new and useful systems and methods for retrieving and analyzing cells, and the inventions disclosed herein provide such useful systems and methods.

BRIEF DESCRIPTION OF THE FIGURES

FIG. 1A is a schematic representation of an embodiment of the system.

FIG. 1B is a schematic representation of an example of the system.

FIG. 9 is a schematic representation of a first example of the method.

DESCRIPTION OF THE PREFERRED EMBODIMENTS

Figure 2:
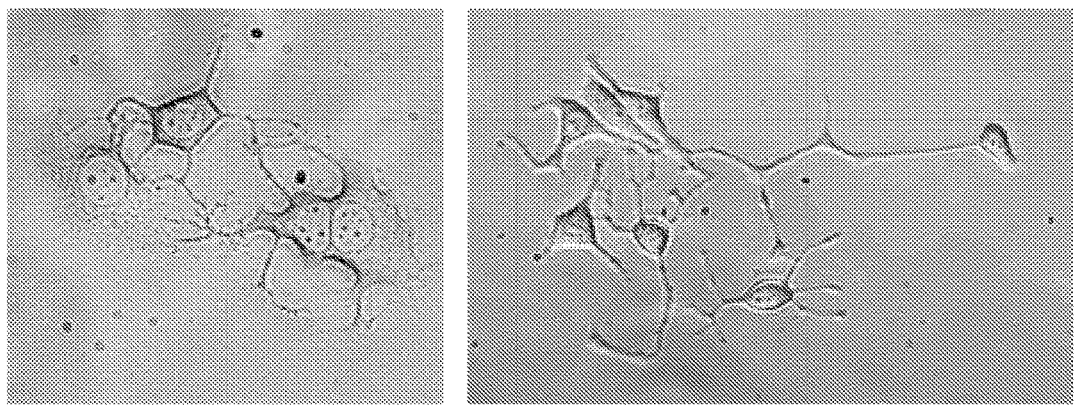
FIG. 2 depicts a first and second micrograph of cells extracted using the system.

The following description of the preferred embodiments of the invention is not intended to limit the invention to these preferred embodiments, but rather to enable any person skilled in the art to make and use this invention.

1. System.

As shown in FIG. 1A, a system 100 for retrieving and analyzing a particle of a set of particles preferably includes: a structural frame 10 supporting: a capture stage 110 that positions a particle capture substrate 200 in a capture mode of the system 100; an imaging subsystem 120 operable to image the particle capture substrate 200 (e.g., wherein the imaging subsystem 120 includes an illumination subsystem 122 operable to transmit light toward the capture stage 110 and cooperating with an optical sensor 126 operable to generate an image dataset of contents of the particle capture substrate 200 in the capture mode); a particle retriever subsystem 130 including a pump 132 fluidly coupled to a particle extractor 134; an actuation subsystem 140 including a first unit 141 coupled the capture stage, a second unit 142 coupled to the imaging subsystem, and a third unit 143 coupled to the particle retriever subsystem; a particle receptacle station 150 hosting a particle receptacle 152; and a control subsystem 160 that, based on a position of the particle at the capture substrate identified from the image dataset, generates commands to retrieve the particle and transmit the particle to the particle receptacle 152.

In more detail (e.g., as shown in FIGS. 1B and/or 7), an embodiment of the system 100 can include: a structural frame 10 supporting: a capture stage 110 defining a broad face 112 that positions a particle capture substrate 200 having a set of particle capture chambers 210 oriented perpendicular to the broad surface 112 in a capture mode of the system 100, the broad surface 112 including an opening 114 toward a closed surface 220 of the capture substrate 200 in the capture mode; an imaging subsystem 120 including: an illumination subsystem 122 operable to transmit light toward the opening 114, a filter subsystem 124 operable to filter light transmitted between the illumination subsystem 122 and the capture substrate 200 in the capture mode, and an optical sensor 126 cooperating with a focusing and optics subsystem 128 that manipulates light transmitted to the optical sensor 126, the optical sensor 126 operable to generate an image dataset of contents of the set of particle capture chambers 210 in the capture mode; a particle retriever subsystem 130 including a pump 132 fluidly coupled to a particle extractor 134 (e.g., capillary tube) having a capture end 135 facing an open surface 230 of the capture substrate in the capture mode; an actuation subsystem 140 including a first unit 141 coupled to the capture stage, a second unit 142 coupled to the imaging subsystem, and a third unit 143 coupled to the particle retriever subsystem; a particle receptacle station 150 hosting a particle receptacle 152; and a control subsystem 160 that, based on a position of the particle at the capture substrate identified from the image dataset, generates commands for aligning the particle extractor 134 with the position of the particle by the actuation subsystem, controlling pressure provided by the pump of the particle retriever subsystem, and transmitting the particle to the particle receptable, thereby retrieving the particle in single-particle format in the capture mode.

In some variations, the system 100 can include: a display 170 in communication with the control subsystem 160, the display operable to render at least one of: control parameters of the system associated with the control subsystem 160 and images derived from the image dataset; and a containment subsystem 180 (e.g., sterile hood) operable to create a sterile environment for sample handling, the containment subsystem 180 configured about the structural frame 10.

The system preferably functions to provide a portable, sterile environment for retrieval of individual cells (e.g., captured in single-cell format) and/or cell clusters. The system preferably enables automated cell localization and identification (e.g., based on image data, such as fluorescence microscopy data), cell extractor 134 (e.g., capillary tube) alignment and insertion, cell extraction (e.g., by aspiration), and/or extracted cell delivery (e.g., to a specified location of a cell receptacle such as a multi-well plate). However, the system can additionally or alternatively perform any other suitable functions.

In a specific example, with a capillary having a 30 μm inner diameter (or other suitable diameter), the system can achieve a throughput of over 90 particles retrieved in 90 minutes, transferring retrieved single cells in a viable state to downstream containers such as well plates (e.g., 96-well plates, well plates of any other suitable format), tubes (e.g., PCR tubes, conicals, etc.), dishes (e.g., Petri dishes), or any other suitable downstream container. As shown in FIG. 2, cells (e.g., MCF7 cells) retrieved in single-cell format from the system can be retrieved in a viable state and grown in culture for further analysis. In the specific example, 5-color fluorescence and brightfield imaging subsystems of the system facilitate positioning of the capillary relative to a target particle/cell of interest for retrieval, in coordination with a computing system for image acquisition, control of illumination, and imaging focus. In the specific example, the system can be placed in a sterile hood for sterile operation; however, variations of the system can alternatively have any other suitable dimension(s) in relation to sterile sample processing.

The structural frame 10 preferably functions to support the other elements of the system 100 (e.g., mechanically coupled to the other elements, such as statically coupled and/or coupled via one or more actuator and/or hinged). For example (e.g., as shown in FIG. 1B), the structural frame 10 can include a member supporting some or all of the focusing and optics subsystem 128 (e.g., by way of a second unit 142 of the actuation subsystem 140), a member supporting the remainder of the imaging subsystem 120, a member supporting the capture stage 110 (e.g., by way of a first unit 141 of the actuation subsystem 140) and optionally the particle receptacle station 150, and a member supporting the particle retriever subsystem 130 (e.g., by way of a third unit 143 of the actuation subsystem 140).

In some embodiments, the structural frame member supporting the particle retriever subsystem 130 includes an arm extending between the actuation subsystem third unit 143 and the particle retriever subsystem 130 (e.g., cantilevered from the third unit 143), which preferably retains the particle extractor substantially in alignment with the optical axis. The are is preferably configured to minimize undesired particle extractor motion (e.g., due to vibration), such as limiting such motion to less than a threshold deviation from the desired position (e.g., less than 10, 5, 2, 1, 0.5, 0.25, or 0.1 microns). For example, the arm can have a natural vibrational mode resulting in a vibrational amplitude of less than the threshold deviation, and/or the system can include one or more vibration dampers between the arm and the third unit 143 (e.g., thereby reducing particle extractor vibrational motion). However, undesired particle extractor motion can additionally or alternatively be minimized in any other suitable manner.

Figure 4A:
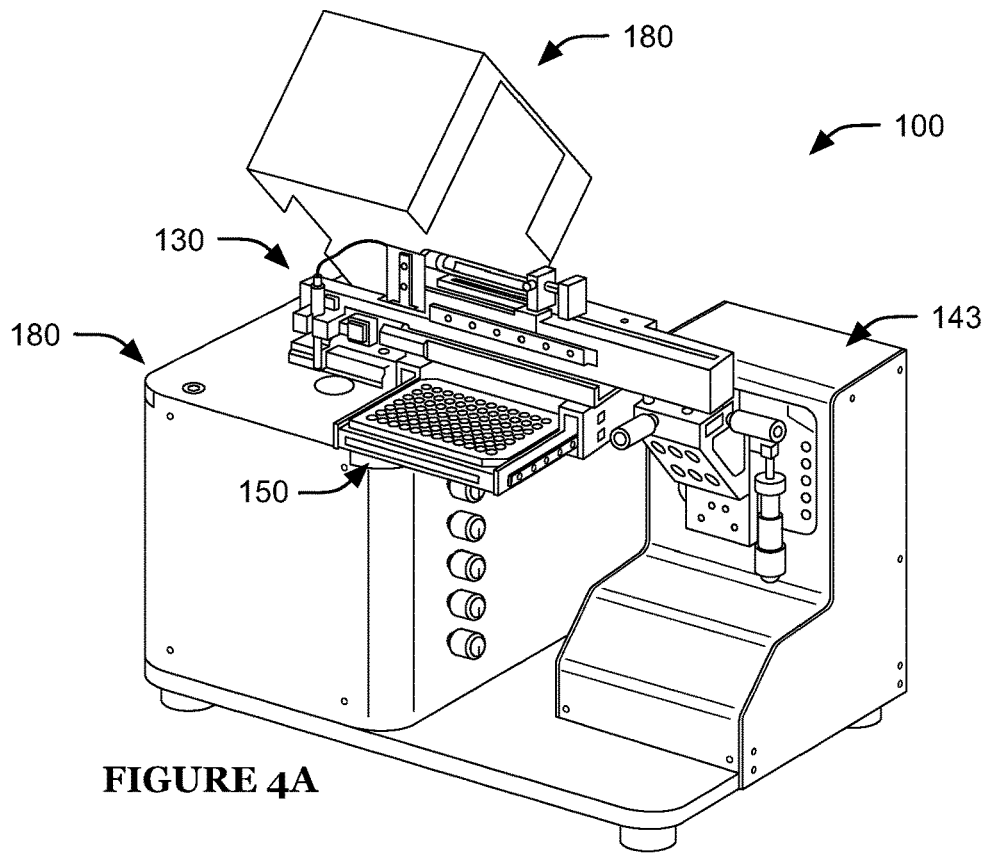
FIGS. 4A-4B are perspective views of a first specific example of the system, with and without a particle receptacle, respectively.
Figure 4B:
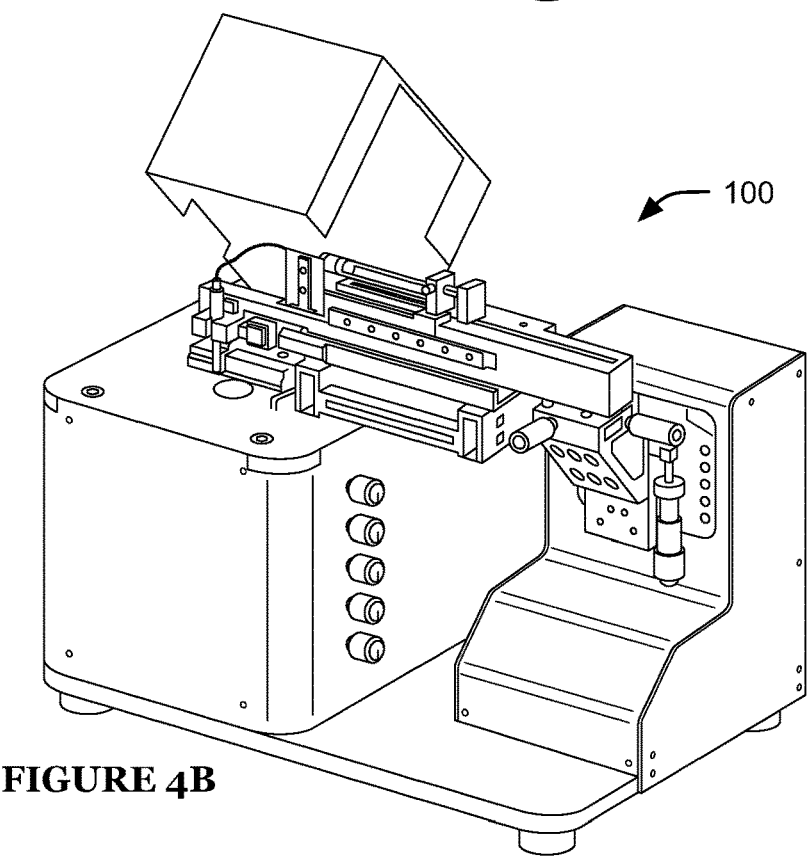

In some embodiments, the structural frame 10 includes multiple independent frame modules (e.g., each supporting elements of distinct subsystems) configured to be attached (e.g., reversibly and/or repeatably attached) to each other, such as by mechanical fasteners (e.g., bolts, clips, clamps, etc.). For example (e.g., as shown in FIGS. 4A-4B), the structural frame 10 can include a first module that supports (e.g., houses, encloses, etc.) the imaging subsystem 120 (and second unit 142 of the actuation subsystem 140) and a second module that supports the capture stage, particle retriever subsystem 130, and remaining elements of the actuation subsystem 140 (e.g., wherein the second module has dimensions between 10 and 50 cm on each side, such as 33×41×25 cm).

The structural frame 10 preferably includes (e.g., is made of) one or more rigid materials, such as metal and/or a rigid polymer. The structural frame 10 can optionally enclose (or substantially enclose) all of some of the other elements of the system (e.g., thereby providing mechanical protection for the elements and/or otherwise isolating the elements from their surroundings). For example, the structural frame 10 can form an optical enclosure (e.g., opaque enclosure, such as a full or partial light-tight enclosure) around some or all of the imaging subsystem 120 (e.g., reducing background readings from ambient light). However, the structural frame 10 can additionally or alternatively include any other suitable elements in any other suitable configuration.

1.1 Capture Stage.

Figure 5A:
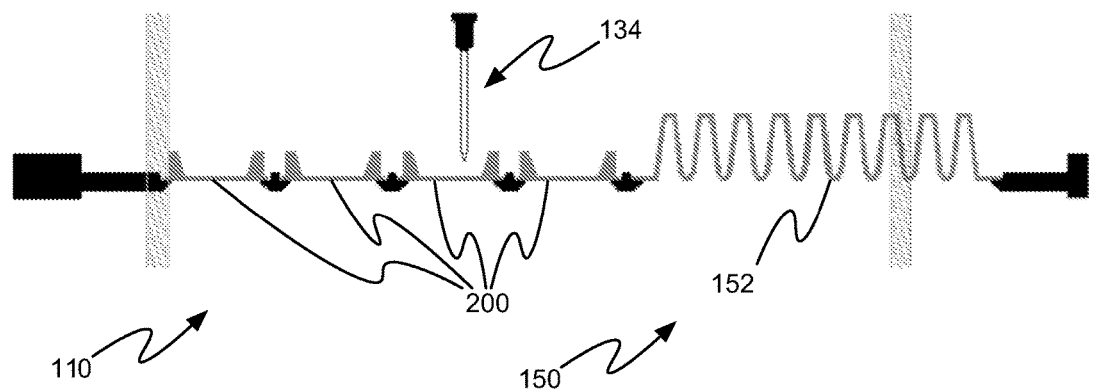
FIG. 5A is a first detail view of a region of FIG. 1B.
Figure 5B:
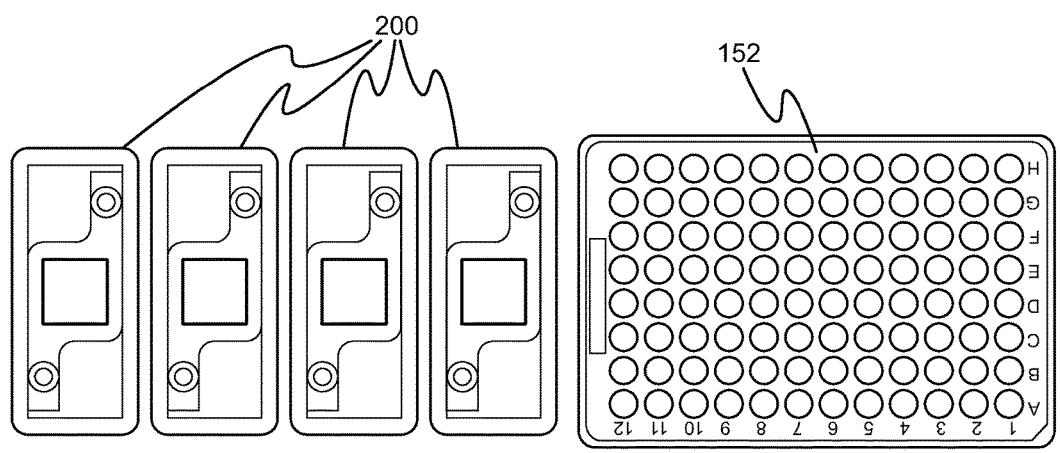
FIG. 5B is a plan view of a specific example of particle capture substrates and a particle receptacle arranged in the system.
Figure 6A:
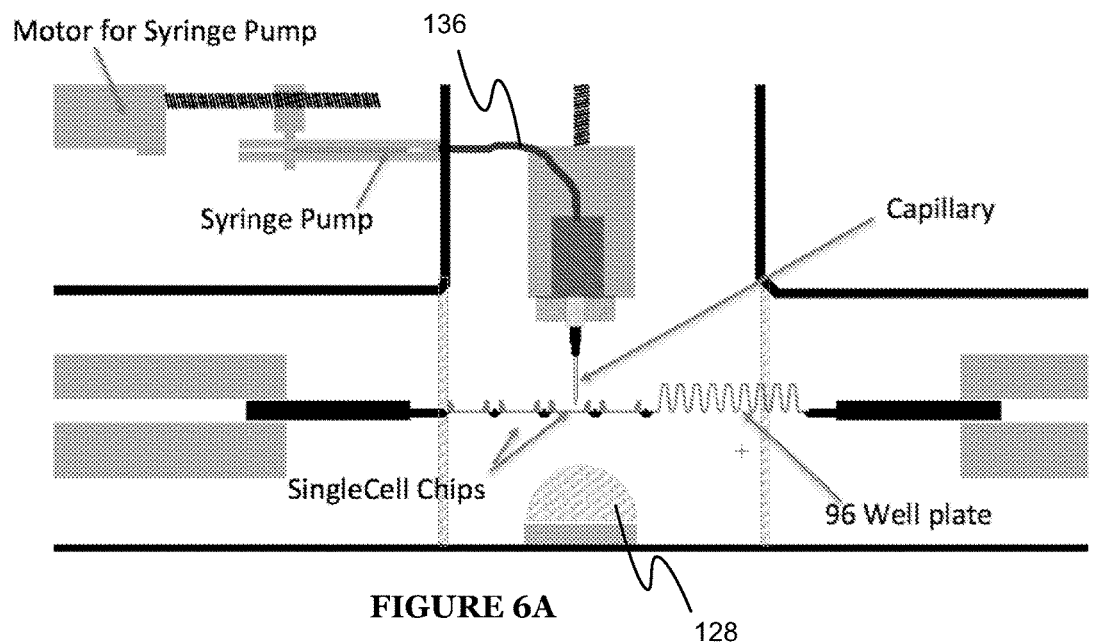
FIGS. 6A-6B are a second and third detail view, respectively, of FIG. 1B.

The capture stage 110 preferably functions to receive and align one or more particle capture substrates 200 (e.g., cell capture devices) relative to the imaging subsystem 120 (e.g., the illumination module 110, focusing and optics subsystem 128, optical sensor 126, etc.), the particle retriever subsystem 130 (e.g., the cell extractor 134), and/or any other suitable elements of the system 100 (e.g., as shown in FIGS. 5A, 5B, and 6A). Such alignment can enable light-based analyses and/or optically-guided retrieval of captured cells (and/or other particles) of interest within the particle capture substrate 200.

The capture stage no preferably defines a broad face 112 coupled to (e.g., retaining, supporting, etc.) one or more particle capture substrates 200. For example, the capture stage no can support a plurality of particle capture substrates 200 (e.g., a closed surface 220 of each substrate 200 retained against the broad face 112 by gravity, by one or more fasteners such as spring clips and/or screws pressing upon an open surface 230 of each substrate 200, etc.). The capture stage no preferably positions the particle capture substrate 200 such that a broad face of the substrate (e.g., the closed surface 220) is against (e.g., substantially coplanar with) the broad face 112 (e.g., in a capture mode). For example, the substrate 200 can be positioned such that a set of particle capture chambers 210 (e.g., defined in the open surface 230, such as normal the open surface 230 and/or closed surface 220) are oriented perpendicular to the broad surface 112. The capture stage 110 preferably does not impede access to the open surface 230 (e.g., to the chambers 210), but can additionally or alternatively include any suitable elements arranged on and/or near the open surface 230.

The broad face 112 preferably includes one or more openings 114. Each opening 114 can provide optical access (e.g., allow light transmission, enable close proximity of an objective lens, etc.) to the closed surface 220 of a substrate 200. Each opening 114 can be a void defined in the broad face 112, a window of transparent material, and/or can be any other suitable opening 114.

The capture stage 110 can additionally or alternatively support the particle receptacle station 150 (e.g., adjacent the particle capture substrates 200). In one example, the capture stage 110 rigidly couples the particle capture substrates 200 and the particle receptacle station 150, enabling coordinated movement of the capture stage 110 and all the rigidly coupled elements (e.g., by the first unit 141 of the actuation subsystem 140). However, the capture stage 110 can additionally or alternatively support any other suitable elements of the system in any other suitable manner.

The capture stage 110 can optionally include elements as described in U.S. patent application Ser. No. 15/430,833, filed 13 Feb. 2017 and titled "System for Imaging Captured Cells", which is herein incorporated in its entirety by this reference (e.g., as described regarding the platform). However, the capture stage 110 can additionally or alternatively include any other suitable elements in any suitable arrangement.

1.2 Imaging Subsystem.

Figure 6B:
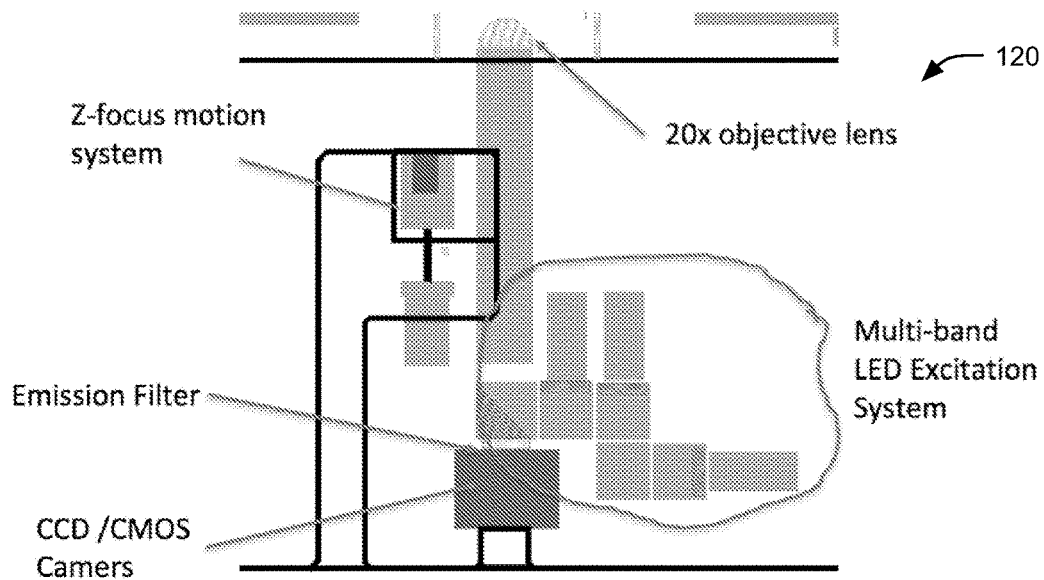
Figure 7:
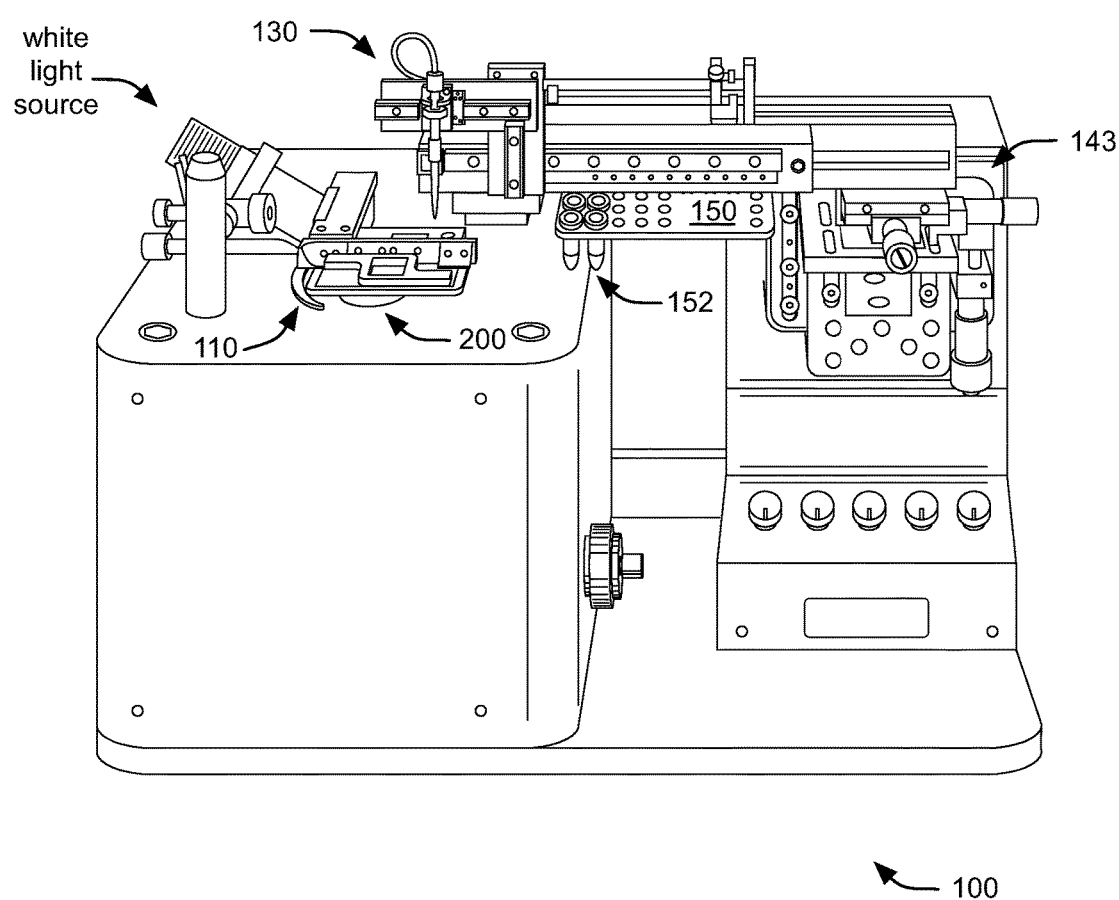
FIG. 7 is a perspective view of a second specific example of the system.

The imaging subsystem 120 preferably includes: an illumination subsystem 122 (e.g., operable to transmit light toward the opening 114), a filter subsystem 124 (e.g., operable to filter light transmitted between the illumination subsystem 122 and the capture substrate 200 in the capture mode), and an optical sensor 126 cooperating with a focusing and optics subsystem 128 that manipulates light transmitted to the optical sensor 126 (e.g., the optical sensor 126 operable to generate an image dataset of contents of the set of particle capture chambers 210 in the capture mode), such as shown in FIG. 6B. The imaging subsystem 120 can include elements such as those described in U.S. patent application Ser. No. 15/430,833, filed 13 Feb. 2017 and titled "System for Imaging Captured Cells", which is herein incorporated in its entirety by this reference.

The imaging subsystem 120 preferably includes a microscope (e.g., inverted microscope) such as a fluorescence microscope. In one example, the illumination subsystem 122 includes a bright-field illumination source (e.g., white light source such as one or more white LEDs, narrow-spectrum and/or single wavelength light source, etc.) and/or a fluorescence light source (e.g., wide-spectrum light source, preferably including ultraviolet and/or infrared wavelengths of light), preferably with adjustable intensity; the filter subsystem 124 includes one or more excitation filters, emission filters, and/or dichroic mirrors (e.g., grouped into one or more filter modules, such as aligned groups including a single excitation filter, dichroic mirror, and emission filter); the optical sensor 126 includes a photodiode comprising a photoelectric material configured to convert electromagnetic energy into electrical signals; and the focusing and optics subsystem 128 includes a lens (e.g., objective lens) configured to focus light from the illumination module onto a target object (e.g., particle capture substrate 200, captured cell, capture end 135 of the cell extractor 134, etc.) at the capture stage 110 (and/or a lens configured to focus light from the target object onto the optical sensor). The lens is preferably oriented substantially normal the broad face 112 (e.g., defines an optical axis substantially normal the broad face 112). The lens (and/or other elements of the focusing and optics subsystem 128) is preferably configured to be moved (e.g., translated substantially along the optical axis) by the second unit 142 of the actuation subsystem 140. However, the imaging subsystem 120 can additionally or alternatively include any other suitable elements in any other suitable arrangement.

1.3 Particle Retriever Subsystem.

The particle retriever subsystem 130 preferably functions to extract at least one of a single cell and a cell cluster (and/or any other suitable particles) from a well of the array. While an individual cell from a single well is preferably selectively removed, the particle retriever subsystem 130 can facilitate simultaneous multiple cell/cell cluster removal from the set of wells. The cell/cell cluster is preferably removed by applying a removal force to the cell. The removal force can be applied by capillary force, but can additionally or alternatively be applied by aspirating the contents out of a well (i.e., using a negative pressure). The removal force can additionally or alternatively be applied by pumping fluid through the set of wells (e.g., by way of a perimeter channel) to provide a positive pressure that drives the cell/cell cluster from the well. In one variation, the pump pressure provided by a pump mechanism at the particle retriever subsystem 130 is less than 10,000 Pa, and in a specific variation, the provided pump pressure is 6,000 Pa. However, any other suitable pump or aspiration pressure can be used.

In some variations, the particle retriever subsystem 130 can comprise a cell extractor 134. The cell extractor 134 functions to selectively remove one or more isolated cells from an addressable location within the system 100. The cell extractor 134 is preferably configured to remove a cell/cell cluster from a single well, but can alternatively be configured to simultaneously remove multiple cells/cell clusters from multiple wells. The particle retriever subsystem 130 is preferably operable in an extraction mode, wherein in the extraction mode the particle retriever subsystem 130 extracts at least one of a set of single cells from a well of the set of wells, along a direction normal to the base surface of the well. In the extraction mode, the fluid delivery module is preferably removed from the substrate; however, the fluid delivery module can alternatively remain coupled to the substrate when the cell removal module is operated in the extraction mode.

In a first variation of the cell extractor 134, the cell extractor 134 is configured to access the set of wells from a direction normal to the open surface 220 (e.g., broad surface) of the substrate 200. The cell extractor 134 preferably removes the cell/cell cluster in a substantially normal direction from the open surface 220 of the substrate 200, but can alternatively remove the cell/cell cluster in an angled direction relative to the open surface 220. The cell extractor 134 preferably defines an interior void, such as a hollow channel (e.g., of a micropipette, capillary tube such as a glass capillary tube, etc.), between a capture end 135 and an outlet (e.g., opposing the capture end 135 across the length of the cell extractor 134) that accesses the set of wells and defines a substantially fluidly isolated volume in fluid communication with one or more wells. The void can include one or more sealing elements at the capture end 135 (e.g., a polymeric coating or adequate geometry) that facilitate fluid seal formation with the well(s) 113. The particle retriever subsystem 130 can optionally include a protective member (e.g., polymer sheath) surrounding a portion of the cell extractor 134 (e.g., surrounding most of an exposed length of the extractor 134, wherein the extractor tip emerges from the sheath to avoid sheath interference with the substrate 200 during tip insertion). The cell extractor 134 preferably tapers from a proximal end to the capture end 135 (e.g., tip), in order to provide an adequate geometry to receive contents of a well into the cell extractor 134; however, the cell extractor 134 can alternatively have any other suitable form. As such, the hollow needle is preferably configured to form a substantially fluidly isolated volume within a well of interest, and a low-pressure generator (e.g., a pump) is then used to aspirate the retained cell/cell cluster out of the well, through the hollow channel, and into a cell collection volume of the cell extractor 134. The void preferably defines a micronscale aperture at the capture end 135, such as an aperture having a characteristic dimension (e.g., diameter, width, inscribed and/or circumscribed circle diameter, etc.) between 1 micron and 500 microns (e.g., between 10 and 100 microns, between 20 and 50 microns, 30 microns, 40 microns, etc.). In one variation, the cell extractor 134 is a micropipette having a height of 200 micrometers and a hollow channel diameter of 25 micrometers; in another variation, the cell extractor 134 is a capillary tube having a channel diameter of 30 micrometers; in a third variation, the cell extractor 134 is a capillary tube having a channel diameter of 150 micrometers. In another variation, the wells of the set of wells are grouped such that each group may be circumscribed by a closed curve in the plane parallel to the broad surface of the substrate, and the cell extractor 134 has an inner diameter that is smaller than the largest chord of the closed curve. In another variation, the inner diameter is smaller than a characteristic dimension (e.g., width, diameter, etc.) of a single well. However, other variations of these specific examples can have any other suitable defining dimensions.

The cell extractor 134 can enable aspiration and/or dispensal of a samples (e.g., particles such as cells, surrounding liquid, etc.) up to a maximum volume (e.g., equal to or less than the volume of the void or a Tillable portion thereof). The maximum volume can be a volume between 0.1 and 500 microliters (e.g., between 1 and 50 microliters, such as 5, 10, or 25 microliters). However, the cell extractor 134 can additionally or alternatively accommodate any other suitable sample volume.

The cell extractor 134 can be manufactured using microfabrication techniques, or can additionally or alternatively be injection molded, laser cut, stamped, or manufactured using any other suitable manufacturing technique. In one variation of hollow needle manufacture, a lumen is preferably etched into a substrate, such as silicon, using etching techniques such as deep reactive ion etching (DRIE), plasma etching, or any other suitable etching method. This step is preferably utilized with a mask that covers the portions of the substrate 105 to be protected. The walls and associated profiles are then preferably manufactured through isotropic etching of the substrate 105 utilizing a corrosive liquid or plasma, but any other suitable isotropic material removal method can be used. A mask is preferably used to protect the puncture end. In a second variation, tubes (e.g., glass tubes, plastic tubes, etc.) can be pulled (e.g., by applying controlled heating to the tube end and pulling the tube under controlled tension) to narrow the tube opening to the desired diameter. Multiple hollow needles are preferably simultaneously manufactured as an array 200, but can alternatively be individually manufactured.

The particle retriever subsystem 130 preferably includes a pump 132 configured to alter pressure within the cell extractor void (e.g., within the hollow channel of the capillary tube). The pump 132 is preferably a positive displacement pump, more preferably a syringe pump, but can additionally or alternatively include any other suitable pump(s). For example, the pump 132 can include a piezoelectric actuator, a diaphragm pump, and/or any other suitable pumping mechanisms.

The pump 132 is preferably controlled by a pump actuator 144, more preferably a motorized actuator (e.g., configured to be controlled by they control subsystem 160), such as described below regarding the actuation subsystem 140. However, the pump 132 can additionally or alternatively be controlled directly (e.g., by manual translation of the syringe pump plunger within the syringe pump barrel, such as by pushing or pulling directly on the plunger by hand).

The pump 132 (e.g., a fluid port of the pump, such as an inlet or outlet) is preferably fluidly coupled to the cell extractor 134 (e.g., to the void) by a tube 136, more preferably a flexible tube. A flexible tube can enable independent movement of the cell extractor 134 with respect to the pump 132 (e.g., during actuation of the actuation subsystem third unit 143; such as during alignment, insertion, and/or removal of the capture end 135). The tube 136 preferably includes (e.g., is made of) a polymeric material (e.g., Teflon, Tygon, polyethylene, etc.), but can additionally or alternatively include metal (e.g., steel, copper, etc.) and/or any other suitable materials. To create effective pumping pressure (e.g., for cell extraction), the dead-volume of the tube 136 is preferably minimized, such as a dead-volume less than a threshold maximum volume (e.g., less than 25, 15, 10, 5, 2, 1, or 0.5 microliters). In one example, the dead-volume is reduced by placing a filler element, such as a wire, inside the tube (e.g., 400 micron diameter wire placed within a tube with a 500 micron inner diameter), thereby occupying a portion of the tubing volume. The tube 136 is preferably a single tube running between the pump 132 and cell extractor 134, but can additionally or alternatively include any suitable fluid manifold and/or other fluidic coupling.

The particle retriever subsystem 130 preferably enables easy removal and/or attachment (e.g., reattachment) of the cell extractor 134 (e.g., capillary tube). This can enable cell extractor cleaning and/or replacement (e.g., of contaminated and/or damaged cell extractors). For example, the cell extractor 134 can be coupled to the tube 136 by a friction fitting (e.g., optionally including hose barbs defined on the cell extractor 134 and/or hose clamps retaining the tube 136 in place on the cell extractor 134). The particle retriever subsystem 130 can include a number of disposable (e.g., one-time use) cell extractors 134, and/or can include one or more cell extractors 134 configured for reuse. However, the particle retriever subsystem 130 can include any other suitable set of cell extractors 134 of any suitable type(s), and/or can include only a single cell extractor 134 (e.g., non-removable cell extractor).

The particle retriever subsystem 130 can, however, include any other suitable cell removal tool, such as that described in U.S. patent application Ser. No. 13/557,510, entitled "Cell Capture System and Method of Use" and filed on 25 Jul. 2012, which is herein incorporated in its entirety by this reference.

Cell removal from the system 100 is preferably automated, but can additionally or alternatively be semi-automated or manual. Furthermore, cell removal can be performed along with cell identification, comprising automatic fixing, permeabilization, staining, imaging, and identification of the cells removed from the set of wells through image analysis (e.g., through visual processing with a processor, by using a light detector, etc.) or in any other suitable manner. The particle retriever subsystem 130 can be configured to facilitate advancement of a cell extractor 134 to a well containing a cell/cell cluster of interest, for instance, with an actuation subsystem. The particle retriever subsystem 130 can additionally or alternatively be configured to facilitate cell removal method selection and/or cell removal tool selection. In another variation, cell identification at the particle retriever subsystem 130 can be semi-automated, and cell retrieval can be automated. For example, cell staining and imaging can be done automatically, wherein identification and selection of the cells of interest can be done manually. In another variation, all steps can be performed manually. However, any combination of automated or manual steps can be used.

1.4 Actuation Subsystem.

The actuation subsystem 140 preferably includes a first unit 141 coupled to (e.g., controlling motion of) the capture stage 110, a second unit 142 coupled to (e.g., controlling motion of) the imaging subsystem 120, a third unit 143 coupled to (e.g., controlling motion of) the particle retriever subsystem 130, and a pump actuator 143 coupled to (e.g., controlling pumping action of) the pump 132.

The first unit 141 preferably enables and/or controls lateral motion (e.g., translation along one or more axes substantially parallel the broad face 112) of the capture stage 110 and/or particle receptacle station 150. For example, the first unit 141 can include an X-axis translator (e.g., controlling lateral translation along a long edge of the capture stage no) and a Y-axis translator (e.g., controlling lateral translation along an axis perpendicular to the X-axis). The first unit 141 can additionally or alternatively enable and/or control translation along an out-of-plane axis (e.g., Z-axis substantially perpendicular the X- and Y-axes, axis substantially normal the broad face 112, axis substantially parallel the optical axis, vertical axis, etc.), lateral rotation (e.g., about the out-of-plane axis), tilt (e.g., rotation about one or more axes substantially parallel the broad face 112, such as the X- and/or Y-axis), and/or any other suitable motion.

The first unit 141 can optionally include an actuator for moving the capture stage 110 and/or particle receptacle station 150 between a particle extraction configuration (e.g., in which the particle capture substrate 200 is aligned with the particle extractor 134 and/or optical axis) and a particle delivery configuration (e.g., in which the particle receptacle station 150 is aligned with the particle extractor 134 and/or optical axis). For example, the capture stage 110 and particle receptacle station 150 (and optionally, other actuators of the first unit 141) can translate along a track and/or rotate about a joint axis (e.g., vertical axis, horizontal axis, etc.) of a cantilever arm to switch between the particle extraction and particle delivery configurations. However, the first unit 141 can additionally or alternatively include any other suitable elements in any other suitable configuration.

The second unit 142 preferably includes a focus actuator enabling and/or controlling imaging subsystem 120 focusing (e.g., by moving the objective lens closer to and/or farther from the imaging target, such as the particle capture substrate 200, its contents, and/or the capture end 135 of the particle extractor). For example, the focus actuator can enable and/or control translation of the objective lens (and/or other optical elements) along the optical axis and/or an axis substantially normal the broad face 112. The focus actuator preferably enables precise control of objective lens movement along the optical axis, such as enabling control to less than a threshold precision (e.g., 10, 50, 75, 100, 150, 400, or 1000 nm). The second unit 142 can optionally include optical element selection actuators, such as rotational and/or translational actuators that move optical elements (e.g., objective lenses, filters, etc.) into and/or out of the optical path. The second unit 142 can additionally or alternatively include lateral translation actuators (e.g., enabling and/or controlling translation of imaging subsystem elements along axes substantially parallel the broad face 112 and/or perpendicular the optical axis), tilt actuators (e.g., enabling and/or controlling rotation of imaging subsystem elements, such as about axes substantially parallel the broad face 112 and/or normal the optical axis), and/or any other suitable actuators.

The third unit 143 preferably includes one or more actuators (e.g., insertion actuator) that enable and/or control out-of-plane motion (e.g., translation along one or more out-of-plane axes not substantially parallel the broad face 112) of the particle extractor 134 (e.g., relative to the capture stage 110 and/or particle receptacle station 150). The out-of-plane axis is preferably an axis substantially normal the broad face 112 and/or the well apertures. However, the out-of-plane axes can additionally or alternatively include a vertical axis, an axis substantially parallel an axis defined by the particle extractor 134 (e.g., defined by the void, such as a central axis of the capillary tube), an axis substantially parallel the optical axis, and/or any other suitable axes. For example, the insertion actuator can control insertion (and/or removal) of the capture end 135 into the substrate 200 (e.g., into the target well; on top of the target well, such as with the capture end 135 in contact with the top surface of the well; etc.), thereby enabling extraction of the well contents (e.g., cell and/or cell cluster, such as a cell captured in single-cell format). The insertion actuator preferably enables precise control of particle extractor motion along the out-of-plane axis (e.g., optical axis), such as enabling control to less than a threshold precision (e.g., 10, 50, 75, 100, 150, 400, or 1000 nm). The insertion actuator can additionally or alternatively be configured to use force sensing and/or stalling of the actuator motor (e.g., to allow precise positioning of the capture end 135 on top of a nanowell).

The third unit 143 can additionally or alternatively include one or more lateral translation actuators. The lateral translation actuators preferably enable and/or control extractor 134 translation along one or more axes substantially parallel the broad face 112 (e.g., the X- and Y-axes) and/or substantially perpendicular the out-of-plane actuator axis. The lateral translation actuators can enable lateral alignment of the particle extractor 134, such as alignment with the optical axis, the target well, a particle receptacle 152 and/or portion thereof (e.g., target well of a multi-well plate), and/or any other suitable element of the system. The third unit 143 can optionally include one or more tilt actuators, which can enable and/or control rotation of the extractor 134 about one or more axes (e.g., lateral axes such as axes substantially parallel the X- and Y-axes). The tilt actuators can enable angular alignment of the particle extractor 134, can enable extraction of particles from wells with different orientations (e.g., including orientations requiring insertion at oblique angles to the broad face 112), and/or can perform any other suitable function.

The third unit 143 can additionally or alternatively include an actuator (e.g., analogous to the actuator described above regarding the first unit 141) for moving the extractor 134 between the particle extraction configuration (e.g., in which the particle extractor 134 is aligned with the particle capture substrate 200 and/or optical axis) and a particle delivery configuration (e.g., in which the particle extractor 134 is aligned with the particle receptacle station 150). For example, the extractor 134 (and optionally, other actuators of the third unit 143, the pump 132 and/or pump actuator 144, and/or any other suitable elements of the system) can translate along a track and/or rotate about a joint axis (e.g., vertical axis, horizontal axis, etc.) of a cantilever arm to switch between the particle extraction and particle delivery configurations. However, the third unit 143 can additionally or alternatively include any other suitable elements in any other suitable configuration.

The actuators of the third unit 143 preferably control motion of the particle extractor 134 but not of the pump 132 (e.g., wherein the extractor 134 is mechanically coupled to the pump 132 by the actuators). However, all or some of the actuators of the third unit 143 can optionally control motion of the pump 132 (e.g., moving the pump 132 and extractor 134 together).

The pump actuator 144 preferably functions to control pumping action (e.g., pressure differential, pumped volume, etc.) of the pump 132. The pump actuator 144 can be used to control aspiration and/or delivery of cell extractor contents (e.g., thereby enabling extraction of particles, such as cells, from the substrate 200 and/or delivery of the extracted particles to the particle receptacle 152). In one example, the particle retriever subsystem 130 can include a linear actuator coupled to the plunger of the syringe pump and configured to translate the plunger within the barrel of the syringe pump (e.g, substantially along a central axis defined by the barrel). The pump actuator 144 (e.g., plunger linear actuator) is preferably controlled by a motor, but can additionally or alternatively be manually actuated (e.g., by a knob) and/or controlled in any other suitable manner. In a second example, the pump actuator 144 includes a piezoelectric actuator (e.g., configured to perform pumping, such as by altering an internal volume of a positive displacement pump) configured to be controlled by electrical control signals (e.g., from the control subsystem 160). However, the actuation subsystem 140 can include any other suitable pump actuators 144 of any other suitable type, which can be controlled (e.g., manually, automatically, such as by the control subsystem 160, etc.) in any suitable manner.

All or some of the actuators preferably enable precise (e.g., sub-micron) control of system element movement. For example, the actuators can include micrometer heads and/or precision drives for precise manual and/or motorized motion control. However, the actuators can additionally or alternatively include any other suitable actuators with any suitable precision. All or some of the actuators can optionally include position detectors such as encoders (e.g., optical, magnetic, etc.; linear, rotary, etc.; absolute, relative, etc.), limit switches, and/or any other suitable position detectors. The position detectors are preferably configured to sample position data and to communicate the position data to other elements of the system (e.g., to the control subsystem 160, to servomotors, etc.). All or some of the actuators can include motors (e.g., stepper motors, servomotors, etc.) and/or any other suitable mechanisms to enable automated control of the actuators (e.g., by the control subsystem 160).

In some variations, the actuation subsystem 140 (e.g., enabling control of capture stage movement, imaging subsystem movement, particle retriever subsystem movement, and/or movement of any other suitable elements of the system) includes elements (and/or enables control) such as described in U.S. patent application Ser. No. 15/430,833, filed 13 Feb. 2017 and titled "System for Imaging Captured Cells", which is herein incorporated in its entirety by this reference (e.g., as described regarding the platform, focusing and optics module, and/or any other suitable elements). For example, the first unit 141 can include actuators such as described regarding the platform, the second unit 142 can include actuators such as described regarding the focusing and optics module, and the third unit 143 and/or pump actuator 144 can include actuators analogous to those described regarding the actuators of the platform and/or focusing and optics module. However, the actuation subsystem 140 can additionally or alternatively include any other suitable actuators.

In some variations, all or some actuators of the actuation subsystem 140 can be configured to be controlled (e.g., be automatically controlled) by the control subsystem 160. For example, the control subsystem 160 can automatically control the first unit 141 (e.g., in order to facilitate automated functions including autofocusing of objects of interest, self-calibration, captured cell and/or particle receptacle alignment with the particle extractor 134, cell capture device interrogation, cell capture device agitation, etc.), second unit 142 (e.g., in order to facilitate automated functions including autofocusing of objects of interest, self-calibration, magnification selection, filter selection, field of view selection, etc.), third unit 143 (e.g., in order to facilitate automated functions including captured cell and/or particle receptacle alignment with the particle extractor 134, particle extractor insertion and/or withdrawal, etc.), pump actuator 144 (e.g., in order to facilitate automated functions including aspiration and/or delivery of fluid within the particle extractor 134, particle extractor priming and/or cleaning, etc.), and/or any other suitable elements of the actuation subsystem 140. However, all or some actuators can additionally or alternatively be semi-automatically controlled and/or manually controlled, such that a user or other entity can manipulate the capture stage 110 in some manner (e.g., using knobs, dials, and/or micrometer heads mechanically coupled to the capture stage 110).

1.5 Particle Receptacle Station.

The particle receptacle station 150 preferably functions to receive and retain one or more particle receptacles 152, and can optionally align the particle receptacles 152 relative to the particle retriever subsystem 130 (e.g., the cell extractor 134), capture stage 110, imaging subsystem 120 (e.g., the illumination module 110, focusing and optics subsystem 128, optical sensor 126, etc.), and/or any other suitable elements of the system 100. For example, the particle receptacle station 150 can support one or more particle receptacles 152 (e.g., retained against the station 150 by gravity and/or by one or more fasteners such as spring clips and/or screws pressing upon each receptacle 152; retained within the station 150 by an inward force exerted along sidewalls of the receptacle 152, such as a compressive force from a friction fit within a rubberized receptacle and/or any other suitable element of the station 150; etc.). The particle receptacles 152 can include tubes (e.g., conical tubes, standard PCR tubes, etc.), multi-well plates (e.g., 96 well plates), Petri dishes, and/or any other suitable receptacles (e.g., receptacles configured to receive and/or contain cells and/or other particles). However, the particle receptacle station 150 can additionally or alternatively include any other suitable elements in any other suitable arrangement.

The particle receptacle station 150 can be rigidly coupled to the capture stage 110 (e.g., as described above), rigidly coupled to the structural frame 10, actuatably coupled (e.g., by one or more actuators of the actuation subsystem 140, such as by the actuators of the first, second, and/or third units, and/or by other actuators enabling independent motion of the particle receptacle station 150) to the structural frame 10 and/or any other suitable element of the system, and/or can be arranged within the system in any other suitable manner.

1.6 Control Subsystem.

The control subsystem 160 preferably functions to control system operation, such as enabling implementation (e.g., automated and/or semi-automated execution) of the methods 300 described below.

The control subsystem 160 can include one or more: processors (e.g., CPU, GPU, microprocessor, etc.), memory and/or data storage modules (e.g., Flash, RAM, hard disk drive, etc.), and/or any other suitable components. The processing system is preferably mounted to the structural frame 10, but can alternatively be mounted to any other suitable component, and/or can be mechanically separate from the other elements of the system 100 (e.g., can be connected to the system by a data connector, can communicate wirelessly with other components of the system, etc.).

The control subsystem 160 is preferably configured to communicate with and/or control other system elements, such as the imaging subsystem 120 and/or actuation subsystem 140. For example, the control subsystem 160 can be coupled (e.g., electrically coupled; otherwise coupled by a coupling capable of transmitting power, control signals, and/or data; etc.) to the optical sensor 126 (enabling activation of the optical sensor 126 and/or receipt of data, such as image data, from the optical sensor 126) and to one or more actuators of the actuation subsystem 140 (e.g., enabling control of the actuators and/or receipt of data, such as position data, from the actuation subsystem 140 position sensors). However, the control subsystem 160 can additionally or alternatively include any other suitable components, be connected to any other suitable elements of the system, and/or perform any other suitable functions.

1.7 Display.

The system 100 can optionally include a display 170. The display 170 is preferably configured to communicate with the control subsystem 160 (e.g., coupled to the control subsystem 160 by a data connection, such as a video data cable; configured to wirelessly receive information from the control subsystem 160; etc.). The display 170 is preferably configured to display one or more of: control parameters of the system associated with the control subsystem 160 and images derived from the image dataset. For example, the display can show images (e.g., near-real time image streams, such as live videos; previously captured images; etc.) captured by the imaging subsystem 120 and/or derivatives thereof, control parameters and/or other information related to system operation (e.g., presented as overlays on the images, presented separate from and/or in place of images, etc.), and/or any other suitable information. The control parameters (e.g., information) presented on the screen (e.g., presented in overlays) can include: positions of system elements (e.g., coordinates, visual indications within and/or outside the image field of view, etc.); current and/or planned motion of system elements; cell identifications such as selected/non-selected cells, cell types (e.g., determined based on fluorescence microscopy data), etc.; target wells for cell retrieval (e.g., from wells of the substrate 200) and/or reception (e.g., at wells of the receptacle 152); retrieval process steps and/or status (e.g., "calibrating", "priming", "identifying cells", "retrieving cell 21 of 40", "washing capillary tube", etc.); and/or any other suitable information. However, the display 170 can additionally or alternatively perform any other suitable function.

1.8 Containment Subsystem.

The containment subsystem 180 preferably functions to create a sterile environment for sample handling (e.g., isolating the system contents, such as the contents of the substrate 200 and/or receptacle 152, from an ambient environment surrounding the containment subsystem 180). In a first embodiment, the containment subsystem 180 is a sterile hood (e.g., biological safety cabinet), wherein the other elements of the system 100 (e.g., the structural frame 10 and attached subsystems) fit within the sterile hood. In this embodiment, the structural frame 10 preferably has dimensions sufficiently small to enable facile placement in (and optionally, removal from) a biological safety cabinet (e.g., less than 10 inches tall×24 inches wide×30 inches deep), but can alternatively have any other suitable dimensions. In a second embodiment, the containment subsystem 180 envelopes the structural frame 10 and attached components (e.g., is attached directly to the exterior of the structural frame 10. In one example (e.g., as shown in FIG. XX), the containment subsystem 180 includes a hinged cover operable between a closed configuration, in which some or all elements of the system (e.g., the capture stage 110 and particle retriever subsystem 130) are enclosed by the cover, and an open configuration which enables user access to the otherwise-enclosed components (e.g., to enable placement and/or removal of system elements, such as particle capture substrates 200, particle extractors 134, etc.). However, the containment subsystem 180 can additionally or alternatively include any other suitable components in any suitable arrangement.

1.9 Particle Capture Substrate.

The particle capture substrate 200 preferably defines a closed surface 220 (e.g., bottom surface) and an open surface 230 (e.g., top surface). The surfaces are preferably broad faces opposing each other (e.g., substantially parallel each other) across the substrate body. The open surface 230 preferably defines a plane, such as a substrate top plane. The substrate 200 preferably defines a set of wells within the substrate body, each well of the set defining: an aperture (e.g., at the plane); a base arranged within the substrate body (e.g., between the aperture and the closed surface 220); and a wall extending from the aperture to the base. Further, the substrate 200 can define a plurality of channels within the substrate body, wherein some or all of the wells are fluidly coupled to one or more adjacent wells one or more of the channels. During cell extractor aspiration at a target well (e.g., during extraction of a cell captured in the target well), these channels can facilitate fluid flow (e.g., convective currents) from adjacent wells, through the target well, and into the cell extractor. This fluid flow can enable, facilitate, and/or urge the captured cell into the cell extractor. In a specific example, the particle capture substrate 200 defines a hexagonal array (e.g., close-packed array) of hexagonal wells with micron-scale width (e.g., 1-100 microns, such as 1, 5, 10, 15, 20, 25, 30, 35, 40, 50, or 60 microns). In this specific example, the wells are subdivided into hexagonal groups of seven wells, wherein the wells of each hexagonal group are fluidly connected by channels, and the inter-group walls separating adjacent hexagonal groups do not allow fluid communication between the hexagonal groups (e.g., do not define channels).

Embodiments, variations, and examples of the particle capture substrate 200 are described in U.S. patent application Ser. No. 13/557,510 titled "Cell Capture System and Method of Use" and filed on 25 Jul. 2012, U.S. patent application Ser. No. 14/289,155 titled "System and Method for Isolating and Analyzing Cells" and filed on 28 May 2014, and U.S. patent application Ser. No. 15/422,222 titled "System and Method for Isolating and Analyzing Cells" and filed on 24 Feb. 2017, which are each incorporated in their entireties by this reference. However, the particle capture substrate 200 can additionally or alternatively include any other suitable elements in any suitable arrangement.

Figure 3A:
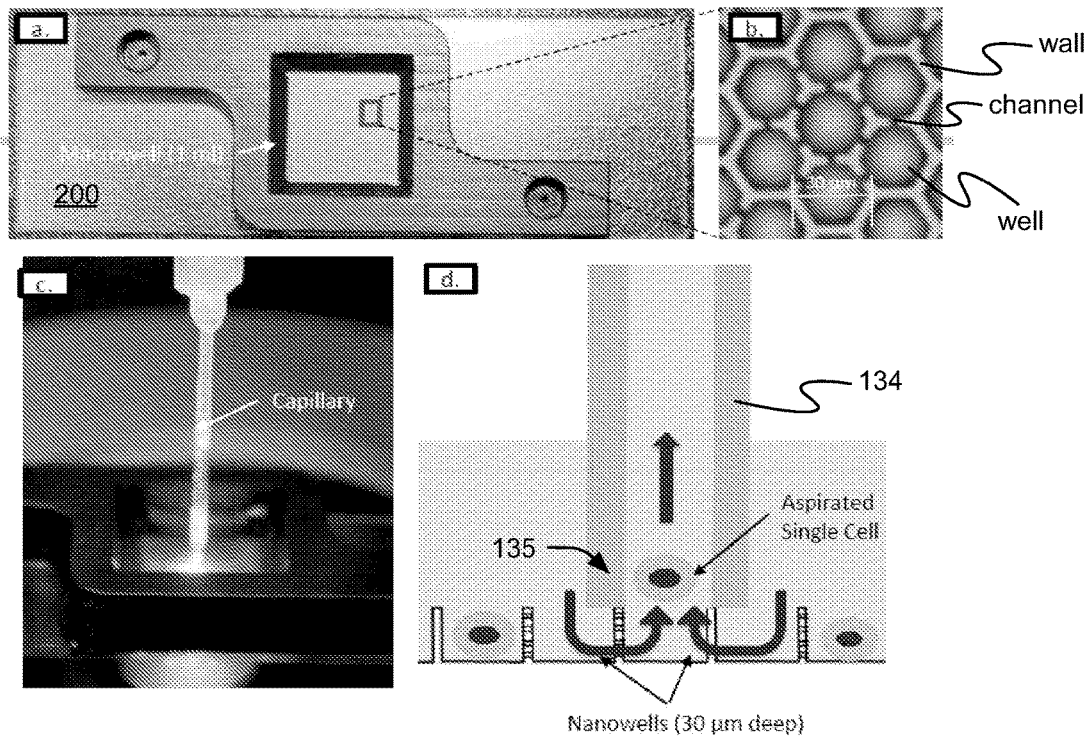
FIG. 3A depicts specific examples of various aspects of the system.
Figure 3B:
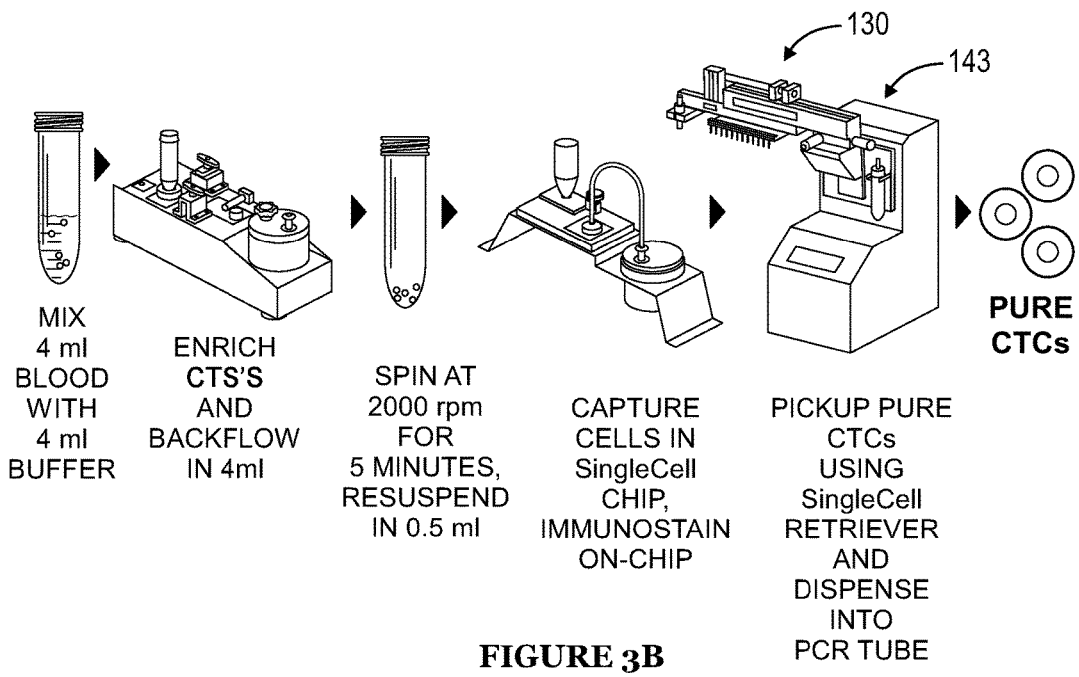
FIG. 3B is a schematic representation of a variation of a method performed using the system.

As shown in FIGS. 3A and 3B, the system 100 can optionally function within (and/or complementary to) a platform for capturing particles from a sample in single-particle format, wherein the platform includes a sample preparation portion operable to process a sample containing a set of particles of interest, and to transmit the processed sample through a particle capture substrate 200 (e.g. microfluidic chip, cell capture substrate, etc.) for capturing the set of particles in single-particle format (and/or in particle clusters). The particles (e.g., cells) can then be retrieved in single-cell format in a viable state for further processing and/or analysis (e.g., in relation to diagnostic applications). In a first embodiment, the system 100 and particle capture platform are integrated (e.g., share a common stage for retaining the particle capture substrate 200), wherein the particle capture substrate 200 remains in place in the particle capture platform during both processed sample transmission and subsequent particle retrieval. In a second embodiment, following processed sample transmission, the particle capture substrate 200 can be removed from the particle capture platform and placed in the capture stage 110 for particle retrieval. However, the system 100 and particle capture platform can additionally or alternatively have any other suitable relationship.

Embodiments, variations, and examples of the sample preparation portion are described in U.S. patent application Ser. No. 14/208,298 titled "System and Method for Capturing and Analyzing Cells" and filed on 13 Mar. 2014, U.S. patent application Ser. No. 15/074,054 titled "System and Method for Capturing and Analyzing Cells" and filed on 18 Mar. 2016, and U.S. patent application Ser. No. 14/208,458 titled "System for Imaging Captured Cells" and filed on 13 Mar. 2014, which are each incorporated in their entireties by this reference. However, the system 100 can additionally or alternatively cooperate with any other suitable platform or platform components.

2. Method.

Figure 8:
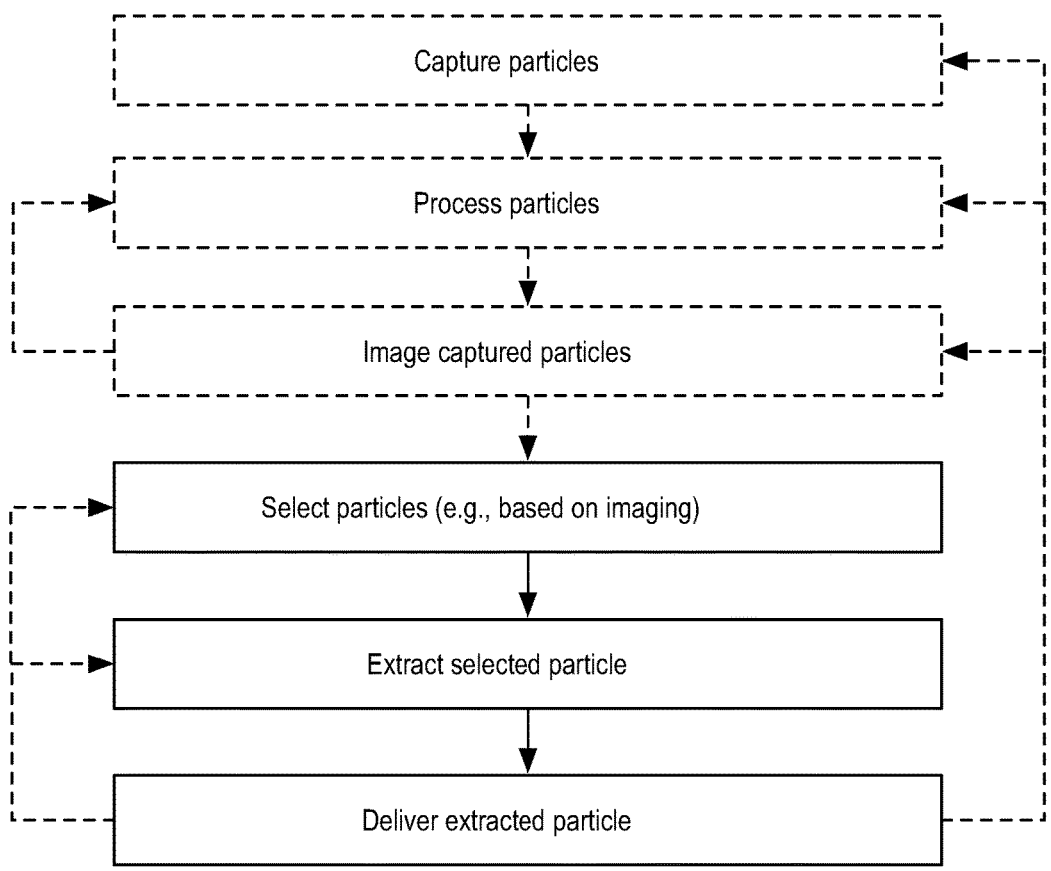
FIG. 8 is a flow chart representation of an embodiment of the method.

A method 300 of captured particle retrieval preferably includes imaging captured particles (e.g., captured within a particle capture substrate 200), selecting captured particles, extracting the selected particles, and delivering the extracted particles (e.g., as shown in FIG. 8). The particles are preferably cells (e.g., live cells), but can additionally or alternatively include any other suitable particles. The method 300 is preferably implemented using the system 100 (and/or particle capture platform) described above, but can additionally or alternatively be implemented using any other suitable mechanisms.

The captured particles are preferably imaged by the imaging subsystem 120 (e.g., using bright-field microscopy, fluorescence microscopy, etc.). Particles are preferably selected (e.g., by the control subsystem 160, by a user, etc.) based on the imaging (e.g., selecting a particular type of cell, wherein the cell type is determined based on fluorescence microscopy). Particle extraction is preferably performed by the particle retriever subsystem 130, more preferably based on image data sampled by the imaging subsystem 120 (e.g., live video showing capture end 135 position relative to the selected cell), which can enable, for example, alignment of the particle extractor 134 over a target well and controlled insertion of the capture end 135 (e.g., into the target well; placement on top of the target well, such as with the capture end 135 in contact with the top surface of the walls defining the target well; etc.). Particle extraction is preferably performed by actuating the pump 132 (e.g., to reduce pressure within the particle extractor, thereby causing aspiration) while the capture end 135 is inserted (e.g., into the target well, on top of the target well, etc.). After extraction, the particle extractor 134 is preferably repositioned at a target region (e.g., target well) of a particle receptacle 152, at which point particle delivery can be achieved by actuating the pump 132 (e.g., to increase pressure within the particle extractor, thereby expelling its contents).

The control subsystem 160 preferably enables automated (and/or semi-automated) performance of the method 300 (and/or elements thereof). For example, the control subsystem 160 can be configured to perform (e.g., based on image data received from the imaging subsystem 120): automated focusing (e.g., by moving the objective lens) on imaging targets such as wells, captured particles, and/or particle extractor capture ends (e.g., capillary tip); automated identification of target cells (e.g., based on fluorescence criteria); automated detection and lateral translation of the capture end (e.g., aligning the capture end with a target well that contains a target cell, aligning the capture end with a destination region of a particle receptacle, etc.); automated placement of the capture end in contact with (e.g., on top of, inserted into, etc.) the target well (e.g., avoiding crashes which can damage the capillary tip, rendering it inoperable to extract cells); automated pump actuation (e.g., to effect aspiration and/or cell ejection); and/or any other suitable elements of the method.

Placing the capture end in contact with the target well can include, for example: focusing on a reference element of the capture substrate, preferably an element of the target well (e.g., top surface of the well); focusing on the particle extractor (e.g., on the capture end, such as the capillary tip); determining a relative distance between the reference element and the particle extractor (e.g., based on the objective lens motion required to switch focus between them); and moving the particle extractor based on the relative distance (e.g., moving toward the target well by an amount equal to the distance, moving by an amount less than the distance, etc.). In one example, focus can be adjusted (e.g., to follow the capture end movement, to switch back and forth between the reference element and the capture end, etc.) during and/or between capture end movement (e.g., repeatedly), and the relative distance determination can be updated accordingly. However, placing the capture end in contact with the target well can additionally or alternatively be performed using any other suitable techniques (e.g., insertion actuator force sensing and/or stalling).

The system 100 can additionally or alternatively support methods (e.g., cell capture, imaging, and/or analysis methods) such as those described in U.S. patent application Ser. No. 15/362,565, titled "System and Method for Capturing and Analyzing Cells" and filed 28 Nov. 2016, U.S. patent application Ser. No. 14/208,298 titled "System and Method for Capturing and Analyzing Cells" and filed on 13 Mar. 2014, U.S. patent application Ser. No. 15/074,054 titled "System and Method for Capturing and Analyzing Cells" and filed on 18 Mar. 2016, and/or U.S. patent application Ser. No. 14/208,458 titled "System for Imaging Captured Cells" and filed on 13 Mar. 2014, which are each incorporated in their entireties by this reference, and/or in any other suitable manner. For example, the method 300 can include capturing particles (e.g., capturing live cells in single-cell format) within wells of a particle capture substrate 200, prior to particle imaging, selection, extraction, and delivery (e.g., as shown in FIG. 9). However, the method 300 can additionally or alternatively include any other suitable elements performed in any other suitable manner.

Figure 10:
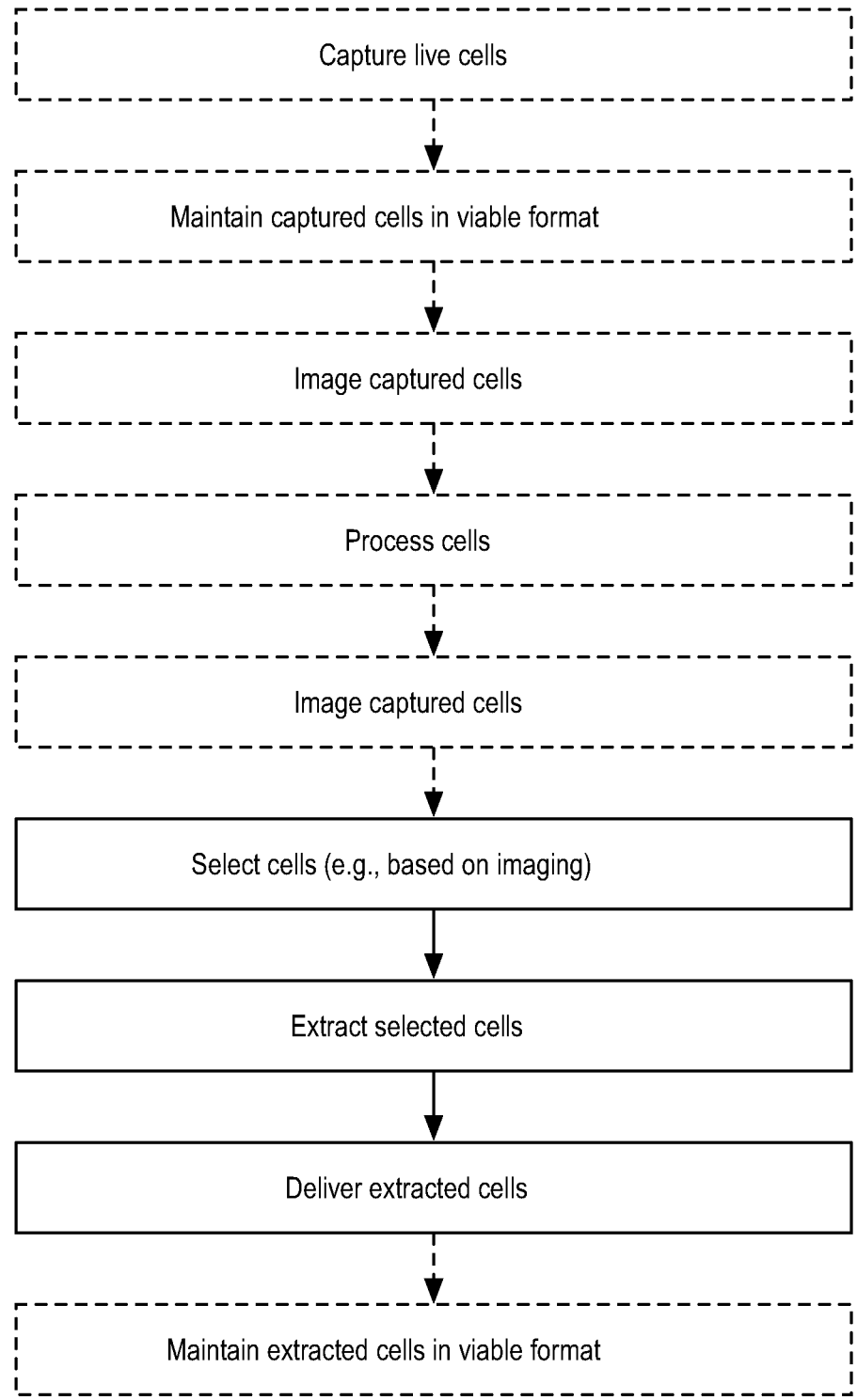
FIG. 10 is a flow chart representation of a second example of the method.

In one embodiment (e.g., as shown in FIG. 10), the method 300 includes: capturing live cells (e.g., in single-cell and/or single-cluster format) in a particle capture substrate 200; maintaining the cells in a viable format (e.g., for multiple days, weeks, etc.); imaging the cells; processing the cells; re-imaging the cells after processing; selecting cells based on the imaging data (e.g., initial imaging and/or re-imaging); extracting the selected cells and delivering the extracted cells to a particle receptacle (e.g., using the system 100 as described above) such as a 96 well plate or a second particle capture substrate; maintaining and/or growing the cells (e.g., culturing the cells) for an extended time period (e.g., days, weeks, etc.); and/or imaging and/or monitoring the extracted cells (e.g., during culturing). In a first example, processing the cells includes treating all captured cells with a set of reagents (e.g., CRISPR reagents). In a second example, processing the cells includes: selecting cells (e.g., a subset of the cells), such as based on the imaging data; and delivering reagents to the selected cells (e.g., the same set of reagents for each selected cell, different sets of reagents for different cells, etc.). In this example, the reagents can be delivered using the particle retriever subsystem (e.g., using the cell extractor; using a different reagent delivery element attached to the particle retriever subsystem, such as in place of the cell extractor; etc.) and/or any other suitable targeted delivery mechanism. For example, the reagent can be delivered using a thinner capillary tube (e.g, thin enough to fit inside the target well, thin enough to penetrate the captured cell, etc.) attached to the particle retriever subsystem, and can optionally include inserting the capillary tube into the target well and/or the captured cell for reagent delivery (e.g., delivering CRISPR reagents directly into the cytosol of the target cell). However, the method 300 can additionally or alternatively include any other suitable elements.

The system 100 and method 300 of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of a processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:
1. A system for cell retrieval, comprising:
a cell capture substrate comprising a first broad face and second broad face opposing the first broad face, the cell capture substrate defining:
a substrate body bounded by a plane, the plane coplanar with the first broad face;
a set of wells within the substrate body, each well of the set defining: an aperture at the plane; a base arranged between the aperture and the second broad face; and a wall extending from the aperture to the base; and a plurality of channels defined within the substrate body, wherein each well of the set is fluidly coupled to an adjacent well of the set by a respective channel of the plurality;

an imaging subsystem configured to sample image data of a target well of the set;

a cell retriever subsystem comprising:
a cell extractor comprising an extractor tip and an outlet, wherein: the cell extractor defines a void between the extractor tip and the outlet; and the extractor tip is positioned proximal the plane; and
a pump fluidly coupled to the void via the outlet;

an actuator configured to translate the cell extractor with respect to the cell capture substrate along an axis substantially normal the plane, the actuator operable to place the extractor tip for fluid communication with the target well; and a control subsystem configured to:
receive the image data from the imaging subsystem;
based on the image data, control a motor of the actuator to position the extractor tip for fluid communication with the target well; and
in response to achieving positioning of the extractor tip for fluid communication with the target well, control the cell retriever to extract a cell from the target well.

2. The system of claim 1, wherein the imaging system comprises:
an optical sensor;
a filter module comprising: an excitation filter and an emission filter;
a light source configured to transmit light through the excitation filter to reach the target well;
a lens defining an optical axis substantially normal the plane, wherein the lens:
focuses light from the excitation filter onto the cell; and
transmits light from the cell, through the emission filter, toward the optical sensor; and
a focus actuator configured to translate the lens substantially along the optical axis.

3. The system of claim 2, wherein:
the filter module further comprises a dichroic mirror configured to bisect intersecting planes defined by the excitation filter and the emission filter; and
the system further comprises a mirror configured to reflect light from the light source into the filter module, such that light from the light source is reflected by 90° twice before reaching the cell capture substrate.

4. The system of claim 1, wherein the pump is a syringe pump fluidly coupled to the void by a flexible tube defining a dead-volume less than 20 microliters.

5. The system of claim 1, wherein the cell extractor is a capillary tube.

6. The system of claim 5, wherein the void defines an aperture at the extractor tip, the aperture defining a width between 10 microns and 50 microns.

7. The system of claim 1, further comprising a cell receptacle, wherein the extractor tip is operable to move from within the target well to within the cell receptacle.

8. The system of claim 1, further comprising a containment subsystem configured to prevent communication of an ambient environment with the set of wells.

9. The system of claim 1, wherein:
the set of wells is divided into subsets of wells, wherein each well of each subset is fluidly connected, by channels of the plurality, to each adjacent well of the subset of wells; and
the walls of each well of each subset prevent fluid communication between each subset and the adjacent subsets of wells.

10. The system of claim 9, wherein:
each subset of wells is circumscribed by a closed curve in the plane; and
an inner diameter of the extractor tip is smaller than a largest chord of the closed curve.

11. The system of claim 1, wherein the cell capture substrate further comprises a manifold defining an inlet and an outlet, wherein the inlet and outlet are fluidly coupled to each well in the set of wells via an interior of the manifold.

12. A system for cell retrieval, comprising:
a cell capture substrate comprising a broad face, the cell capture substrate defining:
a substrate body bounded by a plane, the plane coplanar with the broad face;
a set of wells within the substrate body, each well of the set defining: an aperture at the plane; a base within the substrate body; and a wall extending from the aperture to the base; and
a manifold defining an inlet and an outlet, wherein the inlet and outlet are fluidly coupled to each well in the set of wells via an interior of the manifold;
an optical assembly opposing the plane across the cell capture substrate, the optical assembly defining an optical axis substantially normal the plane; a cell retriever comprising:
a capillary tube positioned proximal the plane; and
a pump fluidly coupled to the capillary tube;
an actuator configured to translate the cell extractor with respect to the cell capture substrate along an axis substantially normal the plane, the actuator operable to place the extractor tip for fluid communication with the target well; and
a control subsystem configured to:
receive the image data from the imaging subsystem;
based on the image data, control a motor of the actuator to place the extractor tip for fluid communication with the target well; and
in response to achieving extractor tip positioning for fluid communication with the target well, control the cell retriever to extract a cell from the target well.

13. The system of claim 12, wherein the cell capture substrate further comprises a plurality of channels defined within the substrate body, wherein each well of the set is fluidly coupled to an adjacent well of the set by a respective channel of the plurality.

14. The system of claim 13, wherein:
the set of wells is divided into subsets of wells, wherein each well of each subset is fluidly connected, by channels of the plurality, to each adjacent well of the subset of wells; and
the walls of each well of each subset prevent fluid communication between each subset and the adjacent subsets of wells.

15. The system of claim 12, further comprising a substrate actuator configured to translate the cell capture substrate along an axis substantially parallel the plane.

16. The system of claim 15, further comprising a cell receptacle mechanically coupled to the cell capture substrate, wherein:
the cell receptacle moves together with the cell capture substrate during actuation of the substrate actuator;
the substrate actuator is operable to position the cell receptacle along a central axis of the capillary tube in a receiving configuration; and in the receiving configuration, the cell retriever is operable to deposit contents of the capillary tube into the cell receptacle.

17. The system of claim 12, wherein the capillary tube defines an inner diameter between 10 microns and 50 microns.

18. The system of claim 12, wherein the optical assembly comprises a fluorescence microscope and an image sensor configured to sample image data from the fluorescence microscope.

19. The system of claim 12, wherein the set of wells contain a plurality of cells in single-cell format.

* * * * *

UNITED STATES PATENT AND TRADEMARK OFFICE
CERTIFICATE OF CORRECTION

Page 1 of 1

PATENT NO. : 10,466,160 B2
APPLICATION NO. : 15/815532
DATED : November 5, 2019
INVENTOR(S) : Kalyan Handique et al.

It is certified that error appears in the above-identified patent and that said Letters Patent is hereby corrected as shown below:

In the Claims

Column 19, Line 30:
In Claim 2, after "comprising:", insert --¶--

Column 20, Line 27:
In Claim 12, after "plane;", insert --¶--

Signed and Sealed this
Third Day of March, 2020

Andrei Iancu
*Director of the United States Patent and Trademark Office*